United States Patent
Usugi et al.

(10) Patent No.: US 9,611,410 B2
(45) Date of Patent: Apr. 4, 2017

(54) ADHESIVE RESIN COMPOSITION, LAMINATE, AND SELF-STRIPPING METHOD

(71) Applicant: MITSUI CHEMICALS TOHCELLO, INC., Chiyoda-ku (JP)

(72) Inventors: Shinichi Usugi, Chiba (JP); Noboru Kawasaki, Sakura (JP); Jun Kamada, Narashino (JP); Takuzo Aida, Bunkyo-ku (JP)

(73) Assignee: MITSUI CHEMICALS TOHCELLO, INC., Tokyo (JP)

( * ) Notice: Subject to any disclaimer, the term of this patent is extended or adjusted under 35 U.S.C. 154(b) by 156 days.

(21) Appl. No.: 14/364,175

(22) PCT Filed: Dec. 7, 2012

(86) PCT No.: PCT/JP2012/007840
§ 371 (c)(1),
(2) Date: Jun. 10, 2014

(87) PCT Pub. No.: WO2013/088686
PCT Pub. Date: Jun. 20, 2013

(65) Prior Publication Data
US 2014/0322474 A1    Oct. 30, 2014

(30) Foreign Application Priority Data
Dec. 14, 2011  (JP) .................................. 2011-273689
Dec. 14, 2011  (JP) .................................. 2011-273692
(Continued)

(51) Int. Cl.
C09J 133/08    (2006.01)
C07D 319/06    (2006.01)
(Continued)

(52) U.S. Cl.
CPC ........... *C09J 133/08* (2013.01); *B32B 43/006* (2013.01); *C07D 319/06* (2013.01); *C09J 7/0217* (2013.01);
(Continued)

(58) Field of Classification Search
CPC .............................. C09J 133/08; C09J 133/10
See application file for complete search history.

(56) References Cited

U.S. PATENT DOCUMENTS 5,326,826 A * 7/1994 Roeschert ............... G03F 7/039
430/169
6,228,552 B1 * 5/2001 Okino ................... G03F 7/0045
430/165
(Continued)

FOREIGN PATENT DOCUMENTS

JP    5-043851 A    2/1993
JP    8-176140 A    7/1996
(Continued)

OTHER PUBLICATIONS

Miyamura et al.: "Controlling Volume Shrinkage in Soft Lithography through Heat-Induced Cross-Linking of Patterned Nanofibers", (Feb. 11, 2011), vol. 133, XP-002738996, ACS Publications, pp. 2840-2843.
(Continued)

*Primary Examiner* — Scott R Walshon
(74) *Attorney, Agent, or Firm* — Buchanan, Ingersoll & Rooney PC

(57) ABSTRACT

An adhesive resin composition includes an expandable sticky polymer having a structure derived from a Meldrum's acid derivative, or a Meldrum's acid derivative represented by the following general formula (1) and an adhesive resin.
(Continued)

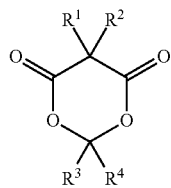

(1)

15 Claims, 1 Drawing Sheet

(30) Foreign Application Priority Data

Jul. 13, 2012 (JP) .................................. 2012-157250
Jul. 13, 2012 (JP) .................................. 2012-157251

(51) Int. Cl.
| | | |
|---|---|---|
| C09J 201/02 | (2006.01) | |
| H01L 21/683 | (2006.01) | |
| C09J 133/14 | (2006.01) | |
| B32B 43/00 | (2006.01) | |
| C09J 7/02 | (2006.01) | |
| H01L 21/56 | (2006.01) | |
| H01L 21/78 | (2006.01) | |
| H01L 23/00 | (2006.01) | |
| C09J 201/08 | (2006.01) | |

(52) U.S. Cl.
CPC ............ *C09J 7/0225* (2013.01); *C09J 133/14* (2013.01); *C09J 201/02* (2013.01); *C09J 201/08* (2013.01); *H01L 21/568* (2013.01); *H01L 21/6835* (2013.01); *H01L 21/6836* (2013.01); *H01L 21/78* (2013.01); *H01L 24/27* (2013.01); *H01L 24/29* (2013.01); *C08L 2203/14* (2013.01); *C09J 2203/326* (2013.01); *H01L 2221/6834* (2013.01); *H01L 2221/68318* (2013.01); *H01L 2221/68327* (2013.01); *H01L 2221/68381* (2013.01); *H01L 2224/27003* (2013.01); *H01L 2224/27436* (2013.01); *H01L 2224/2919* (2013.01); *H01L 2224/83191* (2013.01); *Y10T 156/1153* (2015.01); *Y10T 428/1476* (2015.01)

(56) References Cited

U.S. PATENT DOCUMENTS 6,514,666 B1 * 2/2003 Choi .................... C07D 319/08
  430/270.1
2004/0063870 A1 4/2004 Burns et al.

FOREIGN PATENT DOCUMENTS

| JP | 8-330300 A | 12/1996 | |
|---|---|---|---|
| JP | 11-166164 A | 6/1999 | |
| JP | 2001-200234 A | 7/2001 | |
| JP | 2003-151940 A | 5/2003 | |
| JP | 2003-173989 A | 6/2003 | |
| JP | 2003-173993 A | 6/2003 | |
| JP | 2003-231867 A | 8/2003 | |
| JP | 2003-231871 A | 8/2003 | |
| JP | 2004-043732 A | 2/2004 | |
| JP | 2009-227966 A | 10/2009 | |
| JP | 2009-227996 A | 10/2009 | |
| KR | 10-2001-0034183 A | 4/2001 | |
| WO | WO 99/36484 A1 | 7/1999 | |
| WO | WO 9936484 A1 * | 7/1999 | ............ C08G 59/18 |
| WO | WO 00/17241 A1 | 3/2000 | |
| WO | WO 2010/025983 A1 | 3/2010 | |

OTHER PUBLICATIONS

Yamada et al.: "Toward Environmentally Friendly Photolithographic Materials: A New Class of Water-Soluble Photoresists", (Dec. 24, 2003), vol. 37, XP-002738997, American Chemical Society, pp. 377-384.
Extended European Search Report issued on Jun. 26, 2015, by the European Patent Office in corresponding European Application No. 12857930.7 (7 pages).
Office Action issued by the Korean Patent Office in corresponding Korean Patent Application No. 10-2014-7018878 on Oct. 20, 2015 (6 pages).
International Search Report (PCT/ISA/210) mailed on Feb. 12, 2013, by the Japanese Patent Office as the International Searching Authority for International Application No. PCT/JP2012/007840.
"Development of Heat Resistant Self-Releasing Tape", Journal Polymer, Dec. 2010, pp. 926-927, vol. 59 (With English translation).
Leibfarth et al., "A facile route to ketene-functionalized polymers for general materials applications", Nature Chemistry, Mar. 2010, pp. 207-212, vol. 2.

* cited by examiner

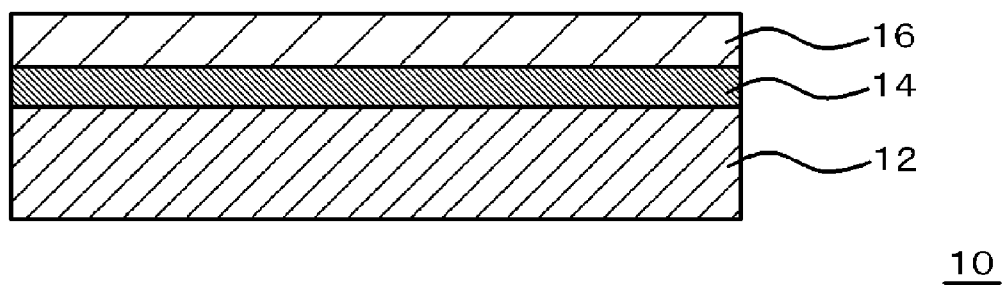

ADHESIVE RESIN COMPOSITION, LAMINATE, AND SELF-STRIPPING METHOD

TECHNICAL FIELD

The present invention relates to an adhesive resin composition, a laminate, and a self-stripping method.

BACKGROUND ART

Examples of the adhesive resin compositions having a self-stripping property in the related art include the following.

In Patent Document 1 (Japanese Unexamined Patent Publication No. 5-43851), a strippable pressure sensitive adhesive, in which an expanding agent is blended with a highly elastic pressure sensitive adhesive, is described. As the expanding agent, an inorganic expanding agent (ammonium carbonate and the like) or an organic expanding agent (an azo-based compound and the like) is used, and further, thermally expandable fine particles formed by microencapsulating the expanding agent, and the like are described. In Patent Document 1, it is described that adhesive strength is reduced by subjecting the expanding agent to a heating treatment to be extended or expanded.

In Patent Document 2 (Japanese Unexamined Patent Publication No. 11-166164), a heating-strippable sticky sheet having a sticky layer including thermally expandable microspheres (microcapsules) having an average particle diameter equal to or more than 18 μm is described.

In Patent Documents 3 and 4 (Japanese Unexamined Patent Publication Nos. 2001-200234 and 2003-151940), it is described that a sticky material including an azide compound is used in a semiconductor preparation process.

In Patent Documents 5 to 8 (Japanese Unexamined Patent Publication Nos. 2003-231871, 2003-173989, 2003-173993, and 2003-231867), a sticky material including a gas generator generating a gas by stimulation is described. As the gas generator, an azo compound and an azide compound are described.

Furthermore, in Non-Patent Document 1 (Journal "Polymer", Vol. 59, December (2010) pp. 926 to 927), a UV sensitive heat-resistant self-stripping tape is described.

The related documents regarding a compound having a Meldrum's acid skeleton or the like include the following.

In Patent Document 9 (Pamphlet of International Publication No. WO 2010/025983), a low outgassing photoresist containing a polymer having a skeleton of Meldrum's acid is described.

In Patent Document 10 (Japanese Unexamined Patent Publication No. 2009-227996), a polymer having a skeleton of Meldrum's acid is described.

In Non-Patent Document 2 (NATURE CHEMISTRY, Vol. 2, March 2010, pp. 207 to 212), it is described that a compound having a skeleton of Meldrum's acid generates carbon dioxide with a ketene by heat.

RELATED DOCUMENT

Patent Document

[Patent Document 1] Japanese Unexamined Patent Publication No. 5-43851
[Patent Document 2] Japanese Unexamined Patent Publication No. 11-166164
[Patent Document 3] Japanese Unexamined Patent Publication No. 2001-200234
[Patent Document 4] Japanese Unexamined Patent Publication No. 2003-151940
[Patent Document 5] Japanese Unexamined Patent Publication No. 2003-231871
[Patent Document 6] Japanese Unexamined Patent Publication No. 2003-173989
[Patent Document 7] Japanese Unexamined Patent Publication No. 2003-173993
[Patent Document 8] Japanese Unexamined Patent Publication No. 2003-231867
[Patent Document 9] Pamphlet of International Publication No. WO 2010/025983
[Patent Document 10] Japanese Unexamined Patent Publication No. 2009-227996

Non-Patent Document

[Non-Patent Document 1] Journal "Polymer" Vol. 59 December (2010) pp. 926 to 927
[Non-Patent Document 2] NATURE CHEMISTRY Vol. 2, March 2010, pp. 207 to 212

DISCLOSURE OF THE INVENTION

However, the technologies described in Patent Documents 1 to 8 have problems in light of the following.

Since an azo compound generates active radical species by applying a stimulation, an adhesive material which is abase is easily decomposed by the active radical species. As a result, the decomposed adhesive material is easily adhered to a body to be adhered to (adhesive residue) or the body to be adhered is easily contaminated during the decomposition.

Moreover, an azide compound is simply decomposed even by applying an impact, and when the decomposition starts, a chain reaction is caused and as a result, it is difficult to control the discharge of a nitrogen gas. Further, it is also thought that the azide compound has a problem due to the generation of active radical species in the similar manner as that of the azo compound.

Furthermore, inorganic expanding agents or microcapsules are not dissolved in an adhesive material to be a base, and therefore, remain on the surface of the adherend during the stripping in some cases.

In addition, in the documents in the related art, regarding these self-strippable adhesives, a compound with a Meldrum's acid skeleton is not described.

In Patent Documents 9 and 10 and Non-Patent Document 2, an example in which a polymer having a skeleton of Meldrum's acid is used as an expandable sticky polymer of a self-strippable adhesive is not described.

The present invention can be seen as follows.

[1] An adhesive resin composition including an expandable sticky polymer having a structure derived from a Meldrum's acid derivative.

[2] The adhesive resin composition as described in [1], in which the Meldrum's acid derivative is represented by the following general formula (1):

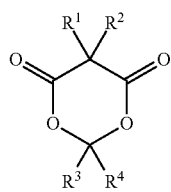

(1)

(In the formula (1), $R^1$ and $R^2$ each independently represent a hydrogen atom, a halogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aryl group, a substituted or unsubstituted arylalkyl group having 7 to 12 carbon atoms, or a substituted or unsubstituted silyl group, and $R^1$ and $R^2$ may be bonded to each other to form a ring structure. $R^3$ and $R^4$ each independently represent a hydrogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, or a substituted or unsubstituted aryl group, and $R^3$ and $R^4$ may be bonded to each other to form a ring structure. At least one of $R^1$, $R^2$, $R^3$, $R^4$, the ring structures formed by the mutual bonding of $R^1$ and $R^2$, and the ring structures formed by the mutual bonding of $R^3$ and $R^4$ has a reactive functional group selected from a vinyl group, an acryloyl group, a methacryloyl group, an epoxy group, an aziridyl group, a thiiranyl group, an oxetanyl group, a thietanyl group, an isocyanate group, an amino group, a sulfone group, a hydroxyl group, a carboxyl group, and an acid anhydride group as a substituent.)

[3] The adhesive resin composition as described in [1] or [2], in which the expandable sticky polymer includes an adhesive resin having a Meldrum's acid derivative bonded through a reactive functional group included in the Meldrum's acid derivative.

[4] The adhesive resin composition as described in [2] or [3], in which the expandable sticky polymer includes:

(a) a constituent unit derived from the Meldrum's acid derivative represented by the general formula (1), in which at least one of $R^1$, $R^2$, $R^3$, $R^4$, the ring structures formed by the mutual bonding of $R^1$ and $R^2$, and the ring structures formed by the mutual bonding of $R^3$ and $R^4$ has a reactive functional group selected from a vinyl group, an acryloyl group, and a methacryloyl group as a substituent, and (b) a constituent unit derived from a (meth)acrylic acid derivative.

[5] The adhesive resin composition as described in [4], in which in the Meldrum's acid derivative, at least one of $R^1$, $R^2$, $R^3$ and $R^4$ is a benzyl group having a vinyl group as a substituent.

[6] The adhesive resin composition as described in any one of [1] to [5], in which the glass transition temperature measured by differential scanning calorimetry is equal to or lower than 40° C.

[7] An adhesive resin composition including:

a Meldrum's acid derivative represented by the following general formula (1):

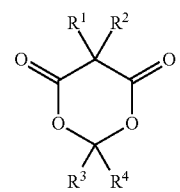

(1)

(In the formula (1), $R^1$ and $R^2$ each independently represent a hydrogen atom, a halogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aryl group, a substituted or unsubstituted arylalkyl group having 7 to 12 carbon atoms, or a substituted or unsubstituted silyl group, and $R^1$ and $R^2$ may be bonded to each other to form a ring structure. $R^3$ and $R^4$ each independently represent a hydrogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, or a substituted or unsubstituted aryl group, and $R^3$ and $R^4$ may be bonded to each other to form a ring structure.); and an adhesive resin.

[8] The adhesive resin composition as described in [7], in which in the general formula (1), $R^1$ and $R^2$ each independently represent a hydrogen atom, an alkyl group having 1 to 4 carbon atoms, or a benzyl group, $R^3$ and $R^4$ each independently represent a hydrogen atom or an alkyl group having 1 to 4 carbon atoms, and $R^3$ and $R^4$ are bonded to each other to form a cyclopentyl group.

[9] The adhesive resin composition as described in [7] or [8], in which the adhesive resin has a glass transition temperature measured by differential scanning calorimetry of equal to or lower than 40° C.

[10] The adhesive resin composition as described in any one of [7] to [9], in which the adhesive resin is an acryl-based pressure sensitive adhesive.

[11] A laminate including:
a base material,
a strippable layer including the adhesive resin composition as described in any one of [1] to [10], formed on the base material, and
an adherend adhered to the strippable layer.

[12] A self-stripping method using a laminate including a base material, a strippable layer having the adhesive resin composition as described in any one of [1] to [6], formed on the base material, and an adherend adhered to the strippable layer, the method including:
a step of heating the laminate to equal to or higher than a temperature at which the Meldrum's acid derivative of an expandable sticky polymer having a structure derived from a Meldrum's acid derivative included in the adhesive resin composition is decomposed, thereby decomposing the compound included in the strippable layer, and reducing the adhesion strength of the strippable layer at the interface between the strippable layer and the adherend.

[13] A self-stripping method using a laminate including a base material, a strippable layer having the adhesive resin composition as described in any one of [7] to [10], formed on the base material, and an adherend adhered to the strippable layer, the method including:

a step of heating the laminate to equal to or higher than a temperature at which the Meldrum's acid derivative is decomposed, and decomposing the Meldrum's acid derivative included in the strippable layer, thereby reducing the adhesion strength of the strippable layer at the interface between the strippable layer and the adherend.

[14] A tape including:

a base material layer; and a strippable layer including the adhesive resin composition as described in any one of [1] to [10], formed on the base material layer.

[15] A method for polishing a substrate, including:

a step of attaching the tape as described in [14] to the backside of a surface to be polished of the substrate through the strippable layer;

a step of polishing the surface to be polished in the substrate; and a step of stripping the tape from the backside by applying heat to the strippable layer of the tape after the polishing step.

[16] A dicing method including:

a step of fixing the adherend onto a support by the adhesive resin composition as described in any one of [1] to [10];

a step of dicing the adherend; and a step of stripping the adherend, which has been made into individual pieces by applying heat, from the support.

[17] A method for preparing a semiconductor package, including:

a step of fixing a semiconductor chip onto a support by the adhesive resin composition as described in any one of [1] to [10];

a step of sealing the semiconductor chip with a resin; and a step of stripping the semiconductor chip sealed with the resin from the support by applying heat.

[18] A plating method including:

a step of attaching the tape as described in [14] to a portion not to be plated in a body to be plated, through the strippable layer;

a step of subjecting the body to be plated to a plating treatment; and a step of stripping the tape by applying heat to the strippable layer of the tape attached to the body to be plated after the plating treatment step.

According to the present invention, an adhesive resin composition which has sufficient adhesion strength during adhesion, can be easily stripped without damaging an adherend during the stripping, and can form a strippable layer having little contamination of the adherend; a laminate having a strippable layer formed of the composition; and a self-stripping method can be provided.

BRIEF DESCRIPTION OF THE DRAWINGS

FIG. 1 is a cross-sectional view showing the configuration of the laminate of the present embodiment.

DESCRIPTION OF EMBODIMENTS

The adhesive resin composition of the present invention will be described below with reference to Embodiments 1 and 2. Further, in the present invention, the terms "adhesive" and "sticky" have the same meanings without specific discretion.

Embodiment 1

Adhesive Resin Composition

The adhesive resin composition of the present embodiment includes an expandable sticky polymer having a structure derived from an expandable compound.

(Expandable Sticky Polymer)

The expandable sticky polymer has a structure derived from a Meldrum's acid derivative which is an expandable compound.

Examples of the expandable sticky polymer include:

(1) a polymer in which a Meldrum's acid derivative is bonded to a polymer chain, and (2) a polymer in which a constituent unit derived from a Meldrum's acid derivative constitutes a part of the polymer chain.

With these expandable sticky polymers, the content of the low molecular compound, which is one of the materials causing the contamination of the body to be adhered, can be reduced.

Hereinafter, these polymers will be described in order.

(1) Expandable Sticky Polymer in which Meldrum's Acid Derivative is Bonded to Polymer Chain As an adhesive resin that serves as a base, ones maintaining the adhesiveness at lower than the heating temperature during the stripping and having heat resistance not generating melting, decomposition, or the like can be used. For example, sticky substance such as the pressure sensitive adhesives (sticky materials) known in the related art can be used.

Examples of the pressure sensitive adhesive include rubber-based pressure sensitive adhesives using a rubber-based polymer such as natural rubber or polyisobutylene rubber, styrene/butadiene rubber, styrene/isoprene/styrene block copolymer rubber, reclaimed rubber, butyl rubber, polyisobutylene rubber, and NBR as a base polymer; silicone-based pressure sensitive adhesives; urethane-based pressure sensitive adhesives; and acryl-based pressure sensitive adhesives. The base material can be constituted with one kind or two or more kinds of components. The acryl-based pressure sensitive adhesives are particularly preferred.

Examples of the acryl-based pressure sensitive adhesives include acryl-based sticky materials having one kind or two or more kinds of acryl-based polymer (homopolymer or copolymer) using an alkyl (meth)acrylate ester as a monomer component as a base polymer. Examples of the alkyl (meth)acrylate ester in the acryl-based sticky material include $C_{1-20}$ alkyl (meth)acrylate esters such as methyl (meth)acrylate, ethyl (meth)acrylate, propyl (meth)acrylate, isopropyl (meth)acrylate, butyl (meth)acrylate, isobutyl (meth)acrylate, s-butyl (meth)acrylate, t-butyl (meth)acrylate, pentyl (meth)acrylate, hexyl (meth)acrylate, heptyl (meth)acrylate, octyl (meth)acrylate, 2-ethylhexyl (meth)acrylate, isooctyl (meth)acrylate, nonyl (meth)acrylate, isononyl (meth)acrylate, decyl (meth)acrylate, isodecyl (meth)acrylate, undecyl (meth)acrylate, dodecyl (meth)acrylate, tridecyl (meth)acrylate, tetradecyl (meth)acrylate, pentadecyl (meth)acrylate, hexadecyl (meth)acrylate, heptadecyl (meth)acrylate, octadecyl (meth)acrylate, nonadecyl (meth)acrylate, and eicosyl (meth)acrylate, and preferably $C_{4-18}$ alkyl (meth)acrylates (linear or branched alkyl) esters.

Furthermore, the acryl-based pressure sensitive adhesives may include units corresponding to other monomer components which can be copolymerizable with the alkyl (meth) acrylate esters for the purpose of improving aggregation power, heat resistance, crosslinkability, or the like, if necessary. Examples of the monomer component include carboxyl group-containing monomers such as acrylic acid, methacrylic acid, carboxyethyl acrylate, carboxypentyl acrylate, itaconic acid, maleic acid, fumaric acid, and crotonic acid; acid anhydride group-containing monomers such as maleic anhydride, and itaconic anhydride; hydroxyl group-containing monomers such as hydroxyethyl (meth)acrylate, hydroxypropyl (meth)acrylate, hydroxybutyl (meth)acrylate, hydroxyhexyl (meth)acrylate, hydroxyoctyl (meth)acrylate, hydroxydecyl (meth)acrylate, hydroxylauryl (meth)acrylate, and (4-hydroxymethylcyclohexyl)methylmethacrylate; sulfonic acid group-containing monomers such as styrenesulfonic acid, allylsulfonic acid, 2-(meth)acrylamide-2-methylpropanesulfonic acid, (meth)acrylamide propanesulfonic acid, sulfopropyl (meth)acrylate, and (meth)acryloyl oxynaphthalenesulfonic acid; phosphoric acid group-containing monomers such as 2-hydroxyethylacryloyl phosphate; (N-substituted)amide-based monomers such as (meth)acryl amide, N,N-dimethyl (meth)acrylamide, N,N-diethyl (meth)acrylamide, N-isopropyl (meth)acrylamide, N-butyl (meth)acrylamide, N-methylol (meth)acrylamide, and N-methylolpropane (meth)acrylamide; aminoalkyl (meth)acrylate-based monomers such as aminoethyl (meth)acrylate, N,N-dimethylaminoethyl (meth)acrylate, and t-butylaminoethyl (meth)acrylate; alkoxyalkyl (meth)acrylate-based monomers such as methoxyethyl (meth)acrylate and ethoxyethyl (meth)acrylate; maleimide-based monomers such as N-cyclohexylmaleimide, N-isopropylmaleimide, N-laurylmaleimide, and N-phenylmaleimide; itaconimide-based monomers such as N-methylitaconimide, N-ethylitaconimide, N-butylitaconimide, N-octylitaconimide, N-2-ethylhexylitaconimide, N-cyclohexylitaconimide, and N-laurylitaconimide; succinimide-based monomers such as N-(meth)acryloyloxymethylene succinimide, N-(meth)acryloyl-6-oxyhexamethylene succinimide, and N-(meth)acryloyl-8-oxyoctamethylene succinimide; vinylesters such as vinyl acetate and vinyl propionate; nitrogen-containing heterocyclic ring-based monomers such as N-vinyl-2-pyrrolidone, N-methylvinylpyrrolidone, N-vinylpyridine, N-vinylpiperidone, N-vinylpyrimidine, N-vinylpiperazine, N-vinylpyrazine, N-vinylpyrrole, N-vinylimidazole, N-vinyloxazole, N-(meth)acryloyl-2-pyrrolidone, N-(meth)acryloylpiperidine, N-(meth)acryloylpyrrolidine, and N-vinylmorpholine; N-vinylcarboxylic acid amides; styrene-based monomers such as styrene and α-methylstyrene; lactam-based monomers such as N-vinylcaprolactam; cyanoacrylate monomers such as acrylonitrile and methacrylonitrile; epoxy group-containing acryl-based monomers such as glycidyl (meth)acrylate; glycol-based acryl ester monomers such as polyethylene glycol (meth)acrylate, polypropylene glycol (meth)acrylate, methoxyethylene glycol (meth)acrylate, and methoxypolypropylene glycol (meth)acrylate; acrylate ester-based monomers having a heterocyclic ring, a halogen atom, a silicon atom, or the like, such as tetrahydrofurfuryl (meth)acrylate, fluorine (meth)acrylate, and silicone (meth)acrylate; polyfunctional monomers such as hexanediol di(meth)acrylate, (poly)ethylene glycol di(meth)acrylate, (poly)propylene glycol di(meth)acrylate, neopentyl glycol di(meth)acrylate, pentaerythritol di(meth)acrylate, trimethylolpropane tri(meth)acrylate, pentaerythritol tri(meth)acrylate, dipentaerythritol hexa(meth)acrylate, epoxyacrylate, polyesteracrylate, urethane acrylate, divinylbenzene, butyl di(meth)acrylate, and hexyl di(meth)acrylate; olefin-based monomers such as isoprene, butadiene, and isobutylene; and vinyl ether-based monomers such as methyl vinyl ether and ethyl vinyl ether. These monomer components may be used alone or in combination of two or more kinds thereof.

For the preparation of the acryl-based pressure sensitive adhesive, any one can be suitably selected from known preparation methods such as solution polymerization, bulk polymerization, emulsion polymerization, and various kinds of radical polymerization. In addition, the obtained adhesive resin may be any one of a random copolymer, a block copolymer, and a graft copolymer.

Furthermore, in the solution polymerization out of the radical polymerization, for example, ethyl acetate, toluene, or the like is used as a polymerization solvent. As a specific example of the solution polymerization, for example, 0.01 parts by weight to 0.2 parts by weight of azobisisobutyronitrile with respect to 100 parts by weight of the total amount of the monomers is added as a polymerization initiator, under an inert gas flow such as nitrogen, and the reaction is carried out usually at about 50° C. to 100° C. for about 8 hours to 30 hours.

A polymerization initiator, a chain transfer agent, an emulsifier, and the like used in the radical polymerization are not particularly limited, and any one can be suitably selected and used.

Examples of the polymerization initiator include azo initiators such as 2,2'-azobisisobutyronitrile, 2,2'-azobis(2-amidinopropane)dihydrochloride, 2,2'-azobis[2-(5-methyl-2-imidazolin-2-yl)propane]dihydrochloride, 2,2'-azobis(2-methylpropionamidine)disulfate, 2,2'-azobis(N,N'-dimethyleneisobutylamidine), and 2,2'-azobis[N-(2-carboxyethyl)-2-methylpropionamidine]hydrate (VA-057, manufactured by Wako Pure Chemical Industries, Ltd.), other persulfates such as potassium persulfate and ammonium persulfate, peroxide initiators such as di(2-ethylhexyl) peroxydicarbonate, di(4-t-butylcyclohexyl)peroxydicarbonate, di-sec-butyl peroxydicarbonate, t-butyl peroxyneodecanoate, t-hexyl peroxypivalate, t-butyl peroxypivalate, dilauroyl peroxide, di-n-octanoyl peroxide, 1,1,3,3-tetramethylbutylperoxy-2-ethyl hexanoate, di(4-methylbenzoyl)peroxide, dibenzoyl peroxide, t-butyl peroxy isobutylate, 1,1-di(t-hexylperoxy)cyclohexane, t-butyl hydroperoxide and hydrogen peroxide, and redox initiators formed by combination of peroxide and a reducing agent, such as a combination of persulfate and sodium hydrogen sulfite, and a combination of peroxide and sodium ascorbate, but are not limited to these examples.

Furthermore, in the case where an organic peroxide is used as a polymerization initiator, it is possible to use the residual organic peroxide, which is not used in a polymerization reaction, in a crosslinking reaction. However, in this case, the residual amount may be determined and then added again, if necessary, and a predetermined amount of the organic peroxide can be used.

The polymerization initiator may be used alone or as a mixture of two or more kinds thereof, and the total content by volume is preferably about 0.005 parts by weight to 1 part by weight, and more preferably about 0.02 parts by weight to 0.6 parts by weight, with respect to 100 parts by weight of the monomers.

In addition, a chain transfer agent may be used in polymerization. By using the chain transfer agent, the molecular weight of the adhesive resin can be adjusted appropriately.

Examples of the chain transfer agent include lauryl mercaptan, glycidyl mercaptan, mercaptoacetic acid, 2-mercaptoethanol, thioglycolic acid, 2-ethylhexyl thioglycolate, and 2,3-dimercapto-1-propanol.

These chain transfer agents may be used alone or as a mixture of two or more kinds thereof, and the total content by volume is about 0.01 parts by weight to 0.4 parts by weight with respect to 100 parts by weight of the monomers.

In addition, examples of the emulsifier used in the case of the emulsion polymerization include anionic emulsifiers such as sodium lauryl sulfate, ammonium lauryl sulfate, sodium dodecyl benzene sulfonate, ammonium polyoxyethylene alkyl ether sulfate, and sodium polyoxyethylene alkyl phenyl ether sulfate, and nonionic emulsifiers such as polyoxyethylene alkyl ether, polyoxyethylene alkyl phenyl ether, polyoxyethylene fatty acid ester, and a polyoxyethylene-polyoxypropylene block polymer. These emulsifiers may be used alone or as a mixture of two or more kinds thereof.

Moreover, specific examples of the emulsifiers introducing radical polymerizable functional groups such as a propenyl group and an allyl ether group, as a reactive emulsifier, include Aqualon HS-10, HS-20, KH-10, BC-05, BC-10, and BC-20 (manufactured by Dai-ichi Kogyo Seiyaku Co., Ltd.), and Adekaria Soap SE10N (manufactured by ADEKA Corporation). Since the reactive emulsifier is taken into the polymer chain after polymerization, water resistance is improved, which is thus preferable. The amount of the emulsifier to be used is 0.3 parts by weight to 5 parts by weight with respect to 100 parts by weight of the monomers, and more preferably 0.5 parts by weight to 1 part by weight, from the viewpoints of polymerization stability or mechanical stability.

The crosslinking reaction of the adhesive resin itself proceeds by heating during the stripping, and thus, an adhesive resin having reduced adhesion performance can be used. In this case, it is necessary to consider that the adhesion is not reduced at lower than the temperature during the stripping.

The Meldrum's acid derivative has a reactive functional group.

Examples of the reactive functional group include a vinyl group, an acryloyl group, a methacryloyl group, an epoxy group, an aziridyl group, a thiiranyl group, an oxetanyl group, a thietanyl group, an isocyanate group, an amino group, a sulfone group, a hydroxyl group, a carboxyl group, and an acid anhydride group.

When it is intended that the Meldrum's acid derivative is bonded to an adhesive resin, the process is conducted in the same manner as a method in which a Meldrum's acid derivative is reacted with a reactive functional group existing in the adhesive resin to form a chemical bond, a method in which the Meldrum's acid derivative is allowed to coexist during the preparation of an adhesive resin to form a chemical bond, a method in which a precursor of a Meldrum's acid derivative is allowed to exist in an adhesive resin and subjected to a chemical reaction to form a Meldrum's acid derivative, or the like.

The Meldrum's acid derivative is represented by the following general formula (1).

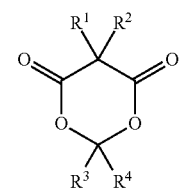

(1)

In the formula (1), $R^1$ and $R^2$ each independently represent a hydrogen atom, a halogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aryl group, a substituted or unsubstituted arylalkyl group having 7 to 12 carbon atoms, or a substituted or unsubstituted silyl group, and $R^1$ and $R^2$ may be bonded to each other to form a ring structure. $R^3$ and $R^4$ each independently represent a hydrogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, or a substituted or unsubstituted aryl group, and $R^3$ and $R^4$ may be bonded to each other to form a ring structure.

Examples of $R^1$, $R^2$, $R^3$ and $R^4$ in the general formula (1) include the following.

Examples of the halogen atom include fluorine, chlorine, bromine, and iodine.

Examples of the alkyl group having 1 to 10 carbon atoms include a methyl group, an ethyl group, a propyl group, an isopropyl group, a butyl group, an isobutyl group, a tertiary butyl group, a pentyl group, a 1-methylbutyl group, a 2-methylbutyl group, a 3-methylbutyl group, a 1,1-dimethylpropyl group, a 2,2-dimethylpropyl group, a 1,2-dimethylpropyl group, a hexyl group, a pentyl group, an octyl group, a nonyl group, a decyl group, a cyclopropyl group, a cyclopropylmethyl group, a cyclopentyl group, a cyclopropylmethyl group, a cyclopentylmethyl group, and a cyclohexylmethyl group.

Examples of the alkenyl group having 2 to 10 carbon atoms include a vinyl group, an isopropenyl group, an allyl group, a methallyl group, a 1-butenyl group, a 3-hexenyl group, a 1-cyclopentenyl group, a 1-cyclohexenyl group, a 2-cyclopentylethenyl group, and a 2-cyclohexylethenyl group.

Examples of the alkynyl group having 2 to 10 carbon atoms include an ethynyl group, a 1-propynyl group, a 2-propynyl group, a 1-butynyl group, a 2-butynyl group, a 3-butynyl group, a 1-pentynyl group, a 2-pentynyl group, a 3-pentynyl group, a 4-pentynyl group, a 1-methyl-2-propynyl group, a 3-methyl-1-butynyl group, a 3,3-dimethyl-1-butynyl group, a 2-cyclopentylethynyl group, and a 2-cyclohexylethynyl group.

Examples of the arylalkyl group having 7 to 12 carbon atoms include a benzyl group, a 1-phenylethyl group, a 2-phenylethyl group, a 1-phenylpropyl group, a 2-phenylpropyl group, a 3-phenylpropyl group, a 1-phenylbutyl group, a 2-phenylbutyl group, a 3-phenylbutyl group, and a 4-phenylbutyl group.

Examples of the aryl group include a phenyl group, a naphthyl group, a biphenyl group, a fluorenyl group, an anthranyl group, a pyridyl group, a triazolyl group, a pyrrole group, a tiinyl group, a pyridyl group, a pyrimidinyl group, an oxazolyl group, an isoxazolyl group, a thiazolyl group, an isothiazolyl group, and an imidazolyl group.

Examples of the substituent in the case where the functional group and the silyl group are substituted include a vinyl group, an acryloyl group, a methacryloyl group, an epoxy group, an aziridyl group, a thiiranyl group, an oxetanyl group, a thietanyl group, an isocyanate group, an amino group, a sulfone group, a hydroxyl group, a carboxyl group, an acid anhydride group, an imide group, a thiol group, and an alkoxy group having 1 to 10 carbon atoms.

The ring structures formed by the mutual bonding of $R^1$ and $R^2$ may be formed, which include carbon atoms bonded with $R^1$ and $R^2$. This also applies to $R^3$ and $R^4$.

Examples of such a ring structure include alicyclic groups, such as cycloalkanes such as cyclopropane, cyclobutane, cyclopentane, cyclohexane, and cycloheptane, cycloalkenes such as cyclopropene, cyclobutene, cyclopentene, cyclohexene, and cycloheptene, and bicyclic alkenes such as norbornene and norbornadiene;

aromatic groups such as phenyl, benzyl, naphthyl, biphenyl, triphenyl, fluorenyl, anthranyl, and phenanthryl; and heterocyclic ring groups such as a pyridyl group, a pyrimidinyl group, a pyridazyl group, a furyl group, a thienyl group, an oxazolyl group, an isoxazolyl group, a thiazolyl group, an isothiazolyl group, a pyrrole group, and an imidazolyl group.

These ring structures may have a substituent, and examples of such a substituent include a vinyl group, an acryloyl group, a methacryloyl group, an epoxy group, an aziridyl group, a thiiranyl group, an oxetanyl group, a thietanyl group, an isocyanate group, an amino group, a sulfone group, a hydroxyl group, a carboxyl group, an acid anhydride group, an imide group, a thiol group, and an alkoxy group having 1 to 10 carbon atoms.

Furthermore, at least one of $R^1$, $R^2$, $R^3$, $R^4$, the ring structures formed by the mutual bonding of $R^1$ and $R^2$, and the ring structures formed by the mutual bonding of $R^3$ and $R^4$ has a reactive functional group selected from a vinyl group, an acryloyl group, a methacryloyl group, an epoxy group, an aziridyl group, a thiiranyl group, an oxetanyl group, a thietanyl group, an isocyanate group, an amino group, a sulfone group, a hydroxyl group, a carboxyl group, and an acid anhydride group as a substituent.

In the present embodiment, $R^1$ and $R^2$ each independently represent a hydrogen atom, an alkyl group having 1 to 4 carbon atoms, a benzyl group, or a phenyl group, and a cyclopropyl group formed by the mutual bonding of $R^1$ and $R^2$ is preferably used.

$R^3$ and $R^4$ each independently represent a hydrogen atom, an alkyl group having 1 to 4 carbon atoms, or a phenyl group, and a cyclopentyl group or a cyclohexyl group formed by the mutual bonding of $R^3$ and $R^4$ is preferably used.

Furthermore, at least one of $R^1$, $R^2$, $R^3$, $R^4$, the ring structures formed by the mutual bonding of $R^1$ and $R^2$, and the ring structures formed by the mutual bonding of $R^3$ and $R^4$ preferably has a reactive functional group selected from a vinyl group, an acryloyl group, and a methacryloyl group as a substituent. Further, at least one of $R^1$, $R^2$, $R^3$ and $R^4$ is preferably a benzyl group having a vinyl group as a substituent.

As the Meldrum's acid derivative used in the present embodiment, one having a structure that can generate a carbon dioxide gas or the like can be used. Specifically, 5-(p-styrylmethyl)-2,2,5-trimethyl-1,3-dioxane-4,6-dione, 5-(p-styrylmethyl)-2-ethyl-2,5-dimethyl-1,3-dioxane-4,6-dione, 8-(p-styrylmethyl)-8-methyl-6,10-dioxaspiro[4,5]decane-7,9-dione, 5-(p-styrylmethyl)-2,2-diethyl-5-methyl-1,3-dioxane-4,6-dione, or the like can be used.

(2) Expandable Sticky Polymer in which Constituent Unit Derived from Meldrum's Acid Derivative Constitutes Part of Polymer Chain In order to synthesize an expandable sticky polymer in which a constituent unit derived from a Meldrum's acid derivative constitutes a part of a polymer chain, the synthesis is conducted by a method in which polymerization is carried out by allowing a Meldrum's acid derivative having a reactive functional group to coexist with a compound having a reactive functional group constituting an adhesive resin, or the like.

The expandable sticky polymer (2) includes:

(a) a constituent unit derived from a Meldrum's acid derivative represented by the general formula (1), in which at least one of $R^1$, $R^2$, $R^3$, $R^4$, the ring structures formed by the mutual bonding of $R^1$ and $R^2$, and the ring structures formed by the mutual bonding of $R^3$ and $R^4$ has a reactive functional group selected from a vinyl group, an acryloyl group, and a methacryloyl group as a substituent, and (b) a constituent unit derived from (meth)acrylic acid derivative.

For the Meldrum's acid derivative, at least one of $R^1$, $R^2$, $R^3$ and $R^4$ is preferably a benzyl group having a vinyl group as a substituent.

The constituent unit derived from a Meldrum's acid derivative (a) can be included in the amount of 0.1 parts by weight to 50 parts by weight, preferably 0.5 parts by weight to 40 parts by weight, and more preferably 1 part by weight to 30 parts by weight, with respect to 100 parts by weight of constituent unit derived from a (meth)acrylic acid derivative.

In addition, the constituent unit derived from a (meth)acrylic acid derivative can use one kind or two or more kinds of (meth)acrylic acid derivative.

Examples of the (meth)acrylic acid derivative include alkyl (meth)acrylate esters, for example, $C_{1-20}$ alkyl (meth)acrylate esters such as methyl (meth)acrylate, ethyl (meth)acrylate, propyl (meth)acrylate, isopropyl (meth)acrylate, butyl (meth)acrylate, isobutyl (meth)acrylate, s-butyl (meth)acrylate, t-butyl (meth)acrylate, pentyl (meth)acrylate, hexyl (meth)acrylate, heptyl (meth)acrylate, octyl (meth)acrylate, 2-ethylhexyl (meth)acrylate, isooctyl (meth)acrylate, nonyl (meth)acrylate, isononyl (meth)acrylate, decyl (meth)acrylate, isodecyl (meth)acrylate, undecyl (meth)acrylate, dodecyl (meth)acrylate, tridecyl (meth)acrylate, tetradecyl (meth)acrylate, pentadecyl (meth)acrylate, hexadecyl (meth)acrylate, heptadecyl (meth)acrylate, octadecyl (meth)acrylate, nonadecyl (meth)acrylate, and eicosyl (meth)acrylate, and preferably $C_{4-18}$ alkyl (meth)acrylate (linear or branched alkyl) esters.

Furthermore, the expandable sticky polymer may contain unit corresponding to other monomer components which are copolymerizable with the alkyl (meth)acrylate ester, if necessary, for the purpose of improving aggregation power, heat resistance, crosslinkability, or the like. Examples of the monomer component include carboxyl group-containing monomers such as acrylic acid, methacrylic acid, carboxyethylacrylate, carboxypentylacrylate, itaconic acid, maleic acid, fumaric acid, and crotonic acid; acid anhydride group-containing monomers such as maleic anhydride, and itaconic anhydride; hydroxyl group-containing monomers such as hydroxyethyl (meth)acrylate, hydroxypropyl (meth)acrylate, hydroxybutyl (meth)acrylate, hydroxyhexyl (meth)acrylate, hydroxyoctyl (meth)acrylate, hydroxydecyl (meth)acrylate, hydroxylauryl (meth)acrylate, and (4-hydroxymethylcyclohexyl)methylmethacrylate; sulfonic acid group-containing monomers such as styrenesulfonic acid, allylsulfonic acid, 2-(meth)acrylamide-2-methylpropanesulfonic acid, (meth)acrylamide propanesulfonic acid, sulfopropyl (meth)acrylate, and (meth)acryloyl oxynaphthalenesulfonic acid; phosphoric acid group-containing monomers such as 2-hydroxyethylacryloyl phosphate; (N-substituted)amide-based monomers such as (meth)acryl amide, N,N-dimethyl (meth)acrylamide, N,N-diethyl (meth)acrylamide, N-isopropyl (meth)acrylamide, N-butyl (meth)acrylamide, N-methylol (meth)acrylamide, and N-methylolpropane (meth)acrylamide; aminoalkyl (meth)acrylate-based monomers such as aminoethyl (meth)acrylate, N,N-dimethylaminoethyl (meth)acrylate, and t-butylaminoethyl (meth)acrylate; alkoxyalkyl (meth)acrylate-based monomers such as methoxyethyl (meth)acrylate and ethoxyethyl (meth) acrylate; maleimide-based monomers such as N-cyclohexylmaleimide, N-isopropylmaleimide, N-laurylmaleimide, and N-phenylmaleimide; itaconimide-based monomers such as N-methylitaconimide, N-ethylitaconimide, N-butylitaconimide, N-octylitaconimide, N-2-ethylhexylitaconimide, N-cyclohexylitaconimide, and N-laurylitaconimide; succinimide-based monomers such as N-(meth)acryloyloxymethylene succinimide, N-(meth)acryloyl-6-oxyhexamethylene succinimide, and N-(meth)acryloyl-8-oxyoctamethylene succinimide; vinylesters such as vinyl acetate and vinyl propionate; nitrogen-containing heterocyclic ring-based monomers such as N-vinyl-2-pyrrolidone, N-methylvinylpyrrolidone, N-vinylpyridine, N-vinylpiperidone, N-vinylpyrimidine, N-vinylpiperazine, N-vinylpyrazine, N-vinylpyrrole, N-vinylimidazole, N-vinyloxazole, N-(meth)acryloyl-2-pyrrolidone, N-(meth)acryloylpiperidine, N-(meth)acryloylpyrrolidine, and N-vinylmorpholine; N-vinylcarboxylic acid amides; styrene-based monomers such as styrene and α-methylstyrene; lactam-based monomers such as N-vinylcaprolactam; cyanoacrylate monomers such as acrylonitrile and methacrylonitrile; epoxy group-containing acryl-based monomers such as glycidyl (meth) acrylate; glycol-based acryl ester monomers such as polyethylene glycol (meth)acrylate, polypropylene glycol (meth) acrylate, methoxyethylene glycol (meth)acrylate, and methoxypolypropylene glycol (meth)acrylate; acrylate ester-based monomers having a heterocyclic ring, a halogen atom, a silicon atom, or the like, such as tetrahydrofurfuryl (meth)acrylate, fluorine (meth)acrylate, and silicone (meth) acrylate; polyfunctional monomers such as hexanediol di(meth)acrylate, (poly)ethylene glycol di(meth)acrylate, (poly)propylene glycol di(meth)acrylate, neopentyl glycol di(meth)acrylate, pentaerythritol di(meth)acrylate, trimethylolpropane tri(meth)acrylate, pentaerythritol tri(meth)acrylate, dipentaerythritol hexa(meth)acrylate, epoxyacrylate, polyesteracrylate, urethane acrylate, divinylbenzene, butyl di(meth)acrylate, and hexyl di(meth)acrylate; olefin-based monomers such as isoprene, butadiene, and isobutylene; and vinyl ether-based monomers such as methyl vinyl ether and ethyl vinyl ether. These monomer components may be used alone or in combination of two or more kinds thereof.

For the preparation of the expandable sticky polymer, any method can be suitably selected from known preparation methods such as solution polymerization, bulk polymerization, emulsion polymerization, and various kinds of radical polymerization. In addition, the obtained adhesive resin may be any one of a random copolymer, a block copolymer, and a graft copolymer.

Furthermore, in the solution polymerization out of the radical polymerization, for example, ethyl acetate, toluene, or the like is used as a polymerization solvent. As a specific example of the solution polymerization, for example, 0.01 parts by weight to 0.2 parts by weight of azobisisobutyronitrile with respect to 100 parts by weight of the total amount of the monomers is added as a polymerization initiator, under an inert gas flow such as nitrogen, and the reaction is usually carried out at about 50° C. to 100° C. for about 8 hours to 30 hours.

The polymerization initiator, the chain transfer agent, the emulsifier, and the like used in the radical polymerization are not particularly limited, and can be suitably selected and used.

Examples of the polymerization initiator include azo initiators such as 2,2'-azobisisobutyronitrile, 2,2'-azobis(2-amidinopropane)dihydrochloride, 2,2'-azobis[2-(5-methyl-2-imidazolin-2-yl)propane]dihydrochloride, 2,2'-azobis(2-methylpropionamidine)disulfate, 2,2'-azobis(N,N'-dimethyleneisobutylamidine), and 2,2'-azobis[N-(2-carboxyethyl)-2-methylpropionamidine]hydrate (VA-057, manufactured by Wako Pure Chemical Industries, Ltd.), other persulfates such as potassium persulfate and ammonium persulfate, peroxide initiators such as di(2-ethylhexyl) peroxydicarbonate, di(4-t-butylcyclohexyl)peroxydicarbonate, di-sec-butyl peroxydicarbonate, t-butyl peroxneodecanoate, t-hexyl peroxypivalate, t-butyl peroxypivalate, dilauroyl peroxide, di-n-octanoyl peroxide, 1,1,3,3-tetramethylbutylperoxy-2-ethyl hexanoate, di(4-methylbenzoyl) peroxide, dibenzoyl peroxide, t-butyl peroxy isobutylate, 1,1-di(t-hexylperoxy)cyclohexane, t-butyl hydroperoxide and hydrogen peroxide, and redox type initiators formed by combination of peroxide and a reducing agent, such as a combination of persulfate and sodium hydrogen sulfite, and a combination of peroxide and sodium ascorbate, but are not limited to these examples.

Furthermore, in the case where organic peroxide is used as a polymerization initiator, it is possible to use the residual organic peroxide, which is not used in a polymerization reaction, in a crosslinking reaction. However, in this case, the residual amount may be determined and then added again, if necessary, and a predetermined amount of the organic peroxide can be used.

The polymerization initiator may be used alone or as a mixture of two or more kinds thereof, and the total content by volume is preferably about 0.005 parts by weight to 1 part by weight, and more preferably about 0.02 parts by weight to 0.6 parts by weight, with respect to 100 parts by weight of the monomers.

In addition, a chain transfer agent may be used in polymerization. By using the chain transfer agent, the molecular weight of the adhesive resin can be adjusted appropriately.

Examples of the chain transfer agent include lauryl mercaptan, glycidyl mercaptan, mercaptoacetic acid, 2-mercaptoethanol, thioglycolic acid, 2-ethylhexyl thioglycolate, and 2,3-dimercapto-1-propanol.

These chain transfer agents may be used alone or as a mixture of two or more kinds thereof, and the total content by volume is about 0.01 parts by weight to 0.4 parts by weight with respect to 100 parts by weight of the monomers.

In addition, examples of the emulsifier used in the case of the emulsion polymerization include anionic emulsifiers such as sodium lauryl sulfate, ammonium lauryl sulfate, sodium dodecyl benzene sulfonate, ammonium polyoxyethylene alkyl ether sulfate, and sodium polyoxyethylene alkyl phenyl ether sulfate, and nonionic emulsifiers such as polyoxyethylene alkyl ether, polyoxyethylene alkyl phenyl ether, polyoxyethylene fatty acid ester, and a polyoxyethylene-polyoxypropylene block polymer. These emulsifiers may be used alone or in combination of two or more kinds thereof.

Moreover, specific examples of the emulsifiers introducing radical polymerizable functional groups such as a propenyl group and an allyl ether group, as a reactive emulsifier, include Aqualon HS-10, HS-20, KH-10, BC-05, BC-10, and BC-20 (manufactured by Dai-ichi Kogyo Seiyaku Co., Ltd.), and Adekaria Soap SE10N (manufactured by ADEKA Corporation). Since the reactive emulsifier is taken into the polymer chain after polymerization, water resistance is improved, which is thus preferable. The amount of the emulsifier to be used is 0.3 parts by weight to 5 parts by weight with respect to 100 parts by weight of the monomers, and more preferably 0.5 parts by weight to 1 part by weight, from the viewpoints of polymerization stability or mechanical stability.

(Other Components)

The adhesive resin composition of the present embodiment may include an organic solvent, a crosslinking agent, a tackifier, a plasticizer, a filler, an aging retardant, an antioxidant, a coloring agent (a pigment, a dye, or the like), a softening agent, a light stabilizer, an ultraviolet ray absorbent, a polymerization inhibitor, an inorganic or organic filler, metal powder, particle-shaped materials, and foil-shaped materials, as a component other than the expandable sticky polymer.

Examples of the organic solvent include methylethylketone, acetone, methylisobutylketone, ethyl acetate, n-butyl acetate, tetrahydrofuran, dioxane, cyclohexanone, n-hexane, n-heptane, cyclohexane, methylcyclohexane, benzene, toluene, xylene, methanol, ethanol, n-propanol, and isopropanol. These solvents may be used alone or as a mixture of two or more kinds thereof.

Examples of the crosslinking agent include an isocyanate-based crosslinking agent, an epoxy-based crosslinking agent, a melamine-based crosslinking agent, a peroxide-based crosslinking agent, a urea-based crosslinking agent, a metal alkoxide-based crosslinking agent, a metal chelate-based crosslinking agent, a metal salt-based crosslinking agent, a carbodiimide-based crosslinking agent, an oxazoline-based crosslinking agent, an aziridine-based crosslinking agent, and an amine-based crosslinking agent, and the isocyanate-based crosslinking agent or the epoxy-based crosslinking agent can be suitably used. Examples of the isocyanate-based crosslinking agent include lower aliphatic polyisocyanates such as 1,2-ethylene diisocyanate, 1,4-butylene diisocyanate, and 1,6-hexamethylene diisocyanate; alicyclic polyisocyanates such as cyclopentylene diisocyanate, cyclohexylene diisocyanate, isophorone diisocyanate, hydrogenated tolylene diisocyanate, and hydrogenated xylene diisocyanate; and aromatic polyisocyanates such as 2,4-tolylene diisocyanate, 2,6-tolylene diisocyanate, 4,4'-diphenylmethane diisocyanate, and xylylene diisocyanate. A trimethylolpropane/tolylene diisocyanate trimeric adduct (Coronate L manufactured by Nippon Polyurethane Industry Co., Ltd.), and a trimethylolpropane/hexamethylene diisocyanate trimeric adduct (Coronate HL manufactured by Nippon Polyurethane Industry Co., Ltd.) can also be used.

Examples of the epoxy-based crosslinking agent include N,N,N',N'-tetraglycidyl-m-xylenediamine, diglycidylaniline, 1,3-bis(N,N-glycidylaminomethyl)cyclohexane, 1,6-hexanediol diglycidyl ether, neopentyl glycol diglycidyl ether, ethylene glycol diglycidyl ether, propylene glycol diglycidyl ether, polyethylene glycol diglycidyl ether, polypropylene glycol diglycidyl ether, sorbitol polyglycidyl ether, glycerol polyglycidyl ether, pentaerythritol polyglycidyl ether, polyglycerol polyglycidyl ether, sorbitan polyglycidyl ether, trimethylolpropane polyglycidyl ether, diglycidyl adipate ester, diglycidyl o-phthalate ester, triglycidyl tris(2-hydroxyethyl)isocyanurate, resorcin diglycidyl ether, bisphenol-S-diglycidyl ether, and an epoxy-based resin having two or more epoxy groups in the molecule.

Examples of the tackifier include rosin derivatives [for example, a rosin, a polymerized rosin, a hydrogenated rosin, derivatives thereof (a rosin ester-based resin, a hydrogenated rosin ester-based resin, and the like), and the like], terpene-based resins (for example, a terpene resin, an aromatic modified terpene resin, a hydrogenated terpene resin, and a terpene phenol resin), phenol-based resins (for example, a phenol-formaldehyde resin and an alkylphenol-formaldehyde resin), petroleum-based hydrocarbon resins [for example, an aliphatic petroleum resin, an aromatic petroleum resin, and an alicyclic petroleum resin formed by hydrogenation of an aromatic petroleum resin (an alicyclic saturated hydrocarbon resin)], styrene-based resins, and chromane-based resins (for example, a coumaronindene resin).

(Method for Preparing Adhesive Resin Composition)

The adhesive resin composition is obtained by mixing the expandable sticky polymer as described above and other components depending on the uses by a method in the related art. As the mixing method, mixing using stirring in a tank, mixing by a kneader, or the like can be used.

(Adhesive Resin Composition)

In the adhesive resin composition obtained by the above-described preparation method, the Meldrum's acid derivative can be included in the amount of 0.1 parts by weight to 50 parts by weight, preferably 0.5 parts by weight to 40 parts by weight, and more preferably 1 part by weight to 30 parts by weight, with respect to 100 parts by weight of the adhesive resin. If the addition amount of the Meldrum's acid derivative is less than the ranges, the amount of the carbon dioxide gas generated is low and the effect of the Meldrum's acid derivative is hardly obtained, and as a result, the stripping effect is low. On the other hand, if the addition amount of the Meldrum's acid derivative is more than the ranges, it causes a part of the strippable layer to remain in the adherend after stripping the adherend, which is a so-called "adhesive residue". That is, if the Meldrum's acid derivative is included in the ranges, the stripping effect is excellent, and thus, an adhesive resin composition having inhibited adhesive residues can be obtained.

For the glass transition temperature of the adhesive resin composition, the glass transition temperature measured by differential scanning calorimetry (DSC) is equal to or lower than 40° C., and preferably equal to or lower than 30° C., and the adhesive resin composition has adhesiveness at ambient temperature.

<Laminate>

As shown in FIG. 1, a laminate 10 of the present embodiment includes a base material 12, a strippable layer (adhesive layer) 14 including the adhesive resin composition of the present embodiment formed on the base material 12, and an adherend 16 adhered to the strippable layer 14.

The strippable layer 14 may have the same shape as a double-sided tape having an adhesive resin composition alone or an adhesive resin composition, a base material A such as a film and a pressure sensitive sticky material B in a layer structure. In that case, it becomes essential that the side of the adhesive resin composition be brought into the adherend 16.

The base material 12 and the adherend 16 may be constituted with various materials according to the uses as described later.

For example, in the case where the laminate 10 is used in a wafer support system, the base material 12 is a hard substrate such as glass and SUS, and the adherend 16 is a silicon substrate (silicon wafer).

In addition, in the case where the laminate 10 is used in the preparation of a ceramic capacitor, the base material 12 is a plastic film or the like, and the adherend 16 is a ceramic capacitor.

The base material 12 used in the present embodiment can be constituted with various materials according to the uses, and examples thereof include plastic base materials such as polyethylene terephthalate (PET) and a polyester film, and porous materials such as paper and non-woven fabric.

The plastic base material is not particularly limited as long as it can be formed into one in the sheet or film shape, and examples thereof include a polyolefin film such as polyethylene, polypropylene, poly-1-butene, poly-4-methyl-1-pentene, an ethylene/propylene copolymer, an ethylene/1-butene copolymer, an ethylene/vinyl acetate copolymer, an ethylene/ethyl acrylate copolymer, and an ethylene/vinyl alcohol copolymer, a polyester film such as polyethylene terephthalate, polyethylene naphthalate, and polybutylene terephthalate, a polyacrylate film, a polystyrene film, a polyamide film such as nylon 6, nylon 6,6, and partially aromatic polyamide, a polyvinyl chloride film, a polyvinylidene chloride film, and a polycarbonate film.

The thickness of the base material 12 is usually 4 μm to 400 μm, preferably about 4 μm to 100 μm, and more preferably about 25 μm to 50 μm.

The plastic base material may be subjected to a releasing or anti-fouling treatment, or an acid treatment with silicone-, fluorine-, long chain alkyl-, or fatty acid amide-based releasing agents, or silica powder, an easy adhesion treatment such as an alkali treatment, a primer treatment, a corona treatment, a plasma treatment, and an ultraviolet ray treatment, or a coating-, kneading-, or deposition-type antistatic treatment, if necessary.

In the case where the strippable layer 14 is only an adhesive resin composition, although varying depending on the uses, it is manufactured by, for example; a method in which an adhesive resin composition is applied to a support such as a separator which has been subjected to a stripping treatment, the solvent and the like are removed by drying, thereby forming a sticky material layer, which is transferred to a base material; a method in which an adhesive resin composition is applied to a base material 12, and the solvent and the like are removed by drying to form a sticky material layer on the base material; or the like.

In order to apply the adhesive resin composition uniformly, one or more kinds of the solvent may be additionally added to the adhesive resin composition.

The preferred range of the film thickness of the strippable layer 14 varies depending on uses, but in the case where the strippable layer 14 is only an adhesive resin composition, the layer is formed in a film thickness of about 0.1 μm to 100 μm, preferably about 1 to 50 μm, and more preferably about 5 μm to 50 μm.

Furthermore, as a method for forming an adhesive resin composition, known methods used for the preparation of sticky sheets are used. Specific examples thereof include methods using a roll coater, a kiss-roll coater, a gravure coater, a reverse coater, a roll brush, a spray coater, a dip-roll coater, a bar coater, a knife coater, an air knife coater, a curtain coater, a lip coater, and a die coater.

In addition, in the case where the adhesive resin composition is exposed to the surface, the strippable layer 14 may be protected with a sheet which has been subjected to a stripping treatment (a strippable sheet, a separator, a strippable liner, or the like, referred to as a separator hereinafter) until being provided for a practical use.

Examples of the constituent material of the separator include plastic films such as polyethylene, polypropylene, polyethylene terephthalate, and a polyester film, porous materials such as paper, cloth, and non-woven fabric, nets, expanded sheets, metal foils, and suitable thin forms of these laminates, and the plastic films are preferably used from the viewpoint of its excellent surface smoothness.

The plastic film is not particularly limited as long as it is a film capable of protecting the adhesive resin composition, and examples thereof include a polyethylene film, a polypropylene film, a polybutene film, a polybutadiene film, a polymethylpentene film, a polyvinyl chloride film, a vinyl chloride copolymer film, a polyethylene terephthalate film, a polybutylene terephthalate film, a polyurethane film, and an ethylene-vinyl acetate copolymer film.

The thickness of the separator is usually 5 μm to 200 μm, and preferably about 5 μm to 100 μm.

The separator may be subjected to a releasing or anti-fouling treatment with a silicone-, fluorine-, long chain alkyl-, or fatty acid amide-based releasing agent, or silica powder, or a coating-, kneading-, or deposition-type antistatic treatment, if necessary. In particular, by appropriately subjecting the surface of the separator to a stripping treatment such as a silicone treatment, a long chain alkyl treatment, and a fluorine treatment, the strippability from the sticky material layer can be further enhanced.

In the case where the strippable layer 14 is a double-sided tape, the method for forming the strippable layer 14 varies depending on the uses, but it is manufactured by a method in which an adhesive resin composition and a pressure sensitive adhesive are applied to a support such as a separator which has been subjected to a stripping treatment, the solvent and the like are removed by drying, thereby forming a sticky material layer, which is transferred to the both sides of a base material A; a method in which an adhesive resin composition and a pressure sensitive adhesive are applied to a base material A, and the solvent and the like are removed by drying to form a sticky material layer on the both sides of the base material A; or the like. At that time, it is necessary that any one adhesive surface of the double-sided tape have the adhesive resin composition of the present embodiment.

Furthermore, as a method for forming the double-sided tape, known methods used for the preparation of sticky sheets are used. Specific examples thereof include methods using a roll coater, a kiss-roll coater, a gravure coater, a reverse coater, a roll brush, a spray coater, a dip-roll coater, a bar coater, a knife coater, an air knife coater, a curtain coater, a lip coater, and a die coater.

Examples of the base material A used in the present embodiment include plastic base materials such as polyethylene terephthalate (PET) and a polyester film and porous materials such as paper and non-woven fabric. The plastic base material is not particularly limited as long as it can be formed into one in the sheet or film shape, and examples thereof include a polyolefin film such as polyethylene, polypropylene, poly-1-butene, poly-4-methyl-1-pentene, an ethylene/propylene copolymer, an ethylene/1-butene copolymer, an ethylene/vinyl acetate copolymer, an ethylene/ethyl acrylate copolymer, and an ethylene/vinyl alcohol copolymer, a polyester film such as polyethylene terephthalate, polyethylene naphthalate, and polybutylene terephthalate, a polyacrylate film, a polystyrene film, a polyamide film such as nylon 6, nylon 6,6, and partially aromatic polyamide, a polyvinyl chloride film, a polyvinylidene chloride film, and a polycarbonate film. The thickness of the base material A is usually 4 µm to 100 µm, and preferably about 25 µm to 50 µm.

The plastic base material may be subjected to a releasing or anti-fouling treatment, or an acid treatment with silicone-, fluorine-, long chain alkyl-, or fatty acid amide-based releasing agents, or silica powder, an easy adhesion treatment such as an alkali treatment, a primer treatment, a corona treatment, a plasma treatment, and an ultraviolet ray treatment, or a coating-, kneading-, or deposition-type antistatic treatment, if necessary.

Although the adhesive resin composition and the pressure sensitive adhesive B are formed on the base material A, the surface of the base material A before the forming or the surface of the adhesive resin composition or the pressure sensitive adhesive B may be protected with a sheet which has been subjected to a stripping treatment (a strippable sheet, a separator, a strippable liner, until being provided for a practical use.

Examples of the constituent material of the separator include plastic films such as polyethylene, polypropylene, polyethylene terephthalate, and a polyester film, porous materials such as paper, cloth, and non-woven fabric, nets, expended sheets, metal foils, and suitable thin forms of these laminates, and the plastic films are preferably used from the viewpoint of its excellent surface smoothness.

The plastic film is not particularly limited as long as it is a film capable of protecting the adhesive resin composition and the pressure sensitive adhesive B, and examples thereof include a polyethylene film, a polypropylene film, a polybutene film, a polybutadiene film, a polymethylpentene film, a polyvinyl chloride film, a vinyl chloride copolymer film, a polyethylene terephthalate film, a polybutylene terephthalate film, a polyurethane film, and an ethylene-vinyl acetate copolymer film.

The thickness of the separator is usually 5 µm to 200 µm, and preferably about 5 µm to 100 µm.

The separator may be subjected to a releasing or anti-fouling treatment with a silicone-, fluorine-, long chain alkyl-, or fatty acid amide-based releasing agent, or silica powder, or a coating-, kneading-, or deposition-type antistatic treatment, if necessary. In particular, by appropriately subjecting the surface of the separator to a stripping treatment such as a silicone treatment, a long chain alkyl treatment, and a fluorine treatment, the strippability from the sticky material layer can be further enhanced.

In the case where the strippable layer 14 is a double-sided tape, the preferred range of the film thickness of the adhesive resin composition varies depending on the uses, and the composition is formed in a film thickness of about 0.1 µm to 100 µm, preferably about 1 µm to 50 µm, and more preferably about 5 µm to 50 µm.

Examples of the pressure sensitive adhesive B include rubber-based pressure sensitive adhesives using a rubber-based polymer such as natural rubber or polyisobutylene rubber, styrene/butadiene rubber, styrene/isoprene/styrene block copolymer rubber, reclaimed rubber, butyl rubber, polyisobutylene rubber, and NBR as a base polymer; silicone-based pressure sensitive adhesives; urethane-based pressure sensitive adhesives; and acryl-based pressure sensitive adhesives, in which an acryl-based polymer having an alkyl ester of an acrylic acid or methacrylic acid as a component is used in a base polymer. The pressure sensitive adhesive can be constituted with one kind or two or more kinds of components as the base material. An acryl-based pressure sensitive adhesive is particularly preferred.

The preferred range of the film thickness of the pressure sensitive adhesive B varies depending on uses, but the pressure sensitive adhesive B is formed in a film thickness of about 5 µm to 50 µm.

For the strippable layer 14, a Meldrum's acid derivative or the like may be included in the adhesive resin composition of the present embodiment as the Meldrum's acid derivative, and the Meldrum's acid derivative and the adhesive resin may be chemically bonded to each other.

Other layers such as an unevenness-absorbing layer and an impact absorbing layer may be included between the base material 12 and the strippable layer 14.

In the case where the strippable layer 14 has the same shape as a double-sided tape having an adhesive resin composition, a base material A such as a film, and a pressure sensitive sticky material B in a layer structure, other layers such as an unevenness-absorbing layer and an impact absorbing layer may be included between the adhesive resin composition and the base material A such as a film, or between the base material A and the pressure sensitive material B.

Examples of the materials for the unevenness-absorbing layer or the impact absorbing layer include rubber-based resin compositions using rubber-based polymers such as natural rubber, polyisobutylene rubber, styrene/butadiene rubber, styrene/isoprene/styrene block copolymer rubber, reclaimed rubber, butyl rubber, polyisobutylene rubber, and NBR as a base polymer; a silicone-based resin composition; a urethane-based resin composition; an acryl-based resin composition using an acryl-based polymer having an alkyl ester of an acrylic acid or a methacrylic acid as a component as a base polymer; and a polyolefin-based resin composition using an ethylene/propylene copolymer, an ethylene/1-butene copolymer, an ethylene/vinyl acetate copolymer, an ethylene/ethyl acrylate copolymer, and an ethylene/vinyl alcohol copolymer, or the like as a base polymer.

The thickness of the unevenness-absorbing layer or the impact absorbing layer may be any thickness which allows the unevenness or impact to be absorbed. The layer is formed in thickness suitable for the uses.

Before the adherend 16 is adhered to the strippable layer 14, the strippable layer 14 may be protected with a sheet which has been subjected to a stripping treatment (a strippable sheet, a separator, or a strippable liner) in order to prevent the strippable layer 14 from exposure.

After the strippable layer 14 is formed, the adherend 16 is adhered to the strippable layer 14. The adherend 16 may be fabricated in advance, or may be formed on a base material after the base material is adhered to the strippable layer 14.

The adherend 16 which has been fabricated in advance may be adhered to the strippable layer 14 or formed on the strippable layer 14. The adherend 16 may be any one of a monolayer structure and a multilayer structure. In the case of the multilayer structure, the multilayer lamination is performed on the strippable layer 14 to form a multilayer structure.

<Self-Stripping Method>

The self-stripping method of the present embodiment is a method using the above-described laminate 10.

Specifically, the method includes a step of heating the laminate 10 to equal to or higher than a temperature at which a Meldrum's acid derivative is decomposed to generate a carbon dioxide gas and the like from the Meldrum's acid derivative included in the strippable layer 14, and thus reduce the adhesion strength of the strippable layer 14 at the interface between the strippable layer 14 and the adherend 16.

When heated to equal to or higher than a predetermined temperature, the Meldrum's acid derivative is decomposed, gases composed of carbon dioxide or acetone are generated and ketenes are also generated. It is thought that the strippable layer 14 is expanded due to the generated gases, and as a result, the contact area between the strippable layer 14 and the adherend 16 is decreased and the adhesion strength is reduced. Further, it is also thought that the pressure of the generated carbon dioxide contributes to the stripping. Further, the generated ketenes have high reactivity and generate curing or condensation of the adhesive resins or the like constituting the strippable layer 14. As a result, it is thought that the elasticity of the adhesive resin is increased and thus, the adhesion strength can be reduced.

By this, the adhesion strength of the strippable layer 14 can be reduced, and thus, the adherend 16 can be easily stripped without damaging the base material 12. By using laminate of the present embodiment, the self-stripping property is excellent and the adherend 16 can be easily stripped in the direction perpendicular to the substrate.

Furthermore, a carbon dioxide gas or the like generated by heating may remain to some degrees in the strippable layer 14 after the stripping.

The amount of the gas generated, which is requisite for the stripping of the adherend 16 appropriately varies depending on the material or structure of the adherend 16, but the adhesive resin composition of the present embodiment can be adjusted with an appropriate amount of a gas generated by changing the addition amount or the structure of the Meldrum's acid derivative.

For example, in the case where a glass plate is used as the base material 12 and the glass plate is adhered through the strippable layer 14 using a silicon wafer as the adherend 16, in order to strip the adherend 16, it is necessary to generate a gas in the amount equal to or more than $2 \times 10^{-3}$ mL/cm², preferably equal to or more than $5 \times 10^{-3}$ mL/cm², more preferably equal to or more than $10 \times 10^{-3}$ mL/cm², and still more preferably equal to or more than $20 \times 10^{-3}$ mL/cm².

The temperature at which the laminate 10 is heated when the adherend 16 is stripped no lower than the temperature at which the Meldrum's acid derivative is decomposed. The temperature is not particularly limited if it is higher than the temperature when the adherend 16 is adhered to the strippable layer 14 or a process temperature required in the preparation step. The upper limit of the heating temperature is about a temperature which does not affect the characteristics of the adherend 16 or the physical properties of a film in the case of using the base material 12 as a resin film. Specifically, the heating temperature is in the range of 50° C. to 350° C., preferably 50° C. to 300° C., and more preferably 50° C. to 250° C.

<Uses>

The laminate 10 of the present embodiment can be preferably used in various uses, which require the adherend 16 to be easily stripped from the strippable layer 14 after the base material 12 and the adherend 16 are adhered through the strippable layer 14 containing a Meldrum's acid derivative. Examples of the uses include a surface protective material or a masking material for prevention of contamination or damage of metallic plates, plastic plates, glass plates, or the like.

Furthermore, the uses of the laminate 10 also include fixing or temporary fixing of parts or articles, or materials or the like as an adherend in the production of various articles, for example, electric parts such as ceramic capacitors, vibrators, and resistivity, display devices such as liquid crystal cells and plasma display, or electronic parts such as solar batteries, thermal heads, printed substrates (inclusive of flexible type ones), and semiconductor chips. Other uses of the laminate 10 include a carrier tape. In the use as a carrier tape, during processing, shipping, or the like, an adherend of a semiconductor, an electronic part, or the like is adhered and held at predetermined intervals in a strippable layer.

Particularly, the laminate 10 is suitable for fixing an adhesive layer of a protective film or a wafer in a semiconductor process, and can be suitably used in Wafer Support System (WSS), Embedded Wafer Level Packages (e-WLP), or the like.

Examples of the uses with the adhesive resin composition of the present embodiment include various uses as described above, and specifically, the adhesive resin composition can be applied in a dicing method, a method for preparing a semiconductor package, or the like.

The dicing method of the present embodiment has a step of fixing an adherend onto a support by the above-described adhesive resin composition, a step of dicing the adherend, and a step of stripping the adherend, which has been made into individual pieces by applying heat, from the support.

First, an adhesive resin composition is applied to a support by a predetermined means, and the adherend is fixed on the applied surface to fix the adherend onto the support.

Examples of the adherend include a silicon wafer, a sapphire substrate, a metallic substrate, and a ceramic capacitor. Examples of the support include a glass plate, a metallic substrate such as SUS and iron, a silicon wafer, and a sapphire substrate. As the dicing method, known methods can be used.

In addition, by applying heat in the above-described temperature range, the adherend, which has been made into individual pieces, for example, a semiconductor chip is stripped from the support.

As described above, the adherend is fixed on the support by the adhesive resin composition of the present embodiment, and it is ensured to protect the adherend during the dicing step, and thus the stripping step can be carried out by a simple method, heating. Accordingly, the production efficiency is excellent. In addition, the contamination of the adherend in the stripping step is reduced, and thus, the yield of the product is enhanced.

The method for preparing the semiconductor package of the present embodiment specifically has a step of fixing a semiconductor chip on a support by the above-described adhesive resin composition, a step of sealing the semiconductor chip with a resin, and a step of applying heat to strip the semiconductor chip sealed with the resin from the support.

First, the adhesive resin composition is applied to the support by a predetermined means, and the semiconductor chip is fixed on the applied surface to fix the semiconductor chip onto the support.

Examples of the support include a glass plate, a metallic substrate such as SUS and iron, a silicon wafer, and a sapphire substrate.

The sealing step can be carried out by methods known in the related art, and further, as the sealing resin, known ones can be used.

Further, by applying heat in the above-described temperature range, the semiconductor chip sealed with a resin can be stripped from the support to obtain a semiconductor package.

As described above, the semiconductor package is fixed on a support by the adhesive resin composition of the present embodiment, and it is ensured to fix the semiconductor package on the support during the sealing step, and thus the stripping step can be carried out by a simple method, heating. Accordingly, the production efficiency is excellent. In addition, the contamination of the semiconductor chip in the stripping step is reduced, and thus, the yield of the product is enhanced.

Moreover, tapes provided with a base material layer, and a strippable layer including the adhesive resin composition of the present embodiment formed on the base material layer can be used in various uses.

The tape in the present embodiment can be obtained by applying the adhesive resin composition of the present embodiment on a base material film to form a strippable layer.

Further, the base material film which becomes a base material layer includes polyolefin-based resins such as polyethylene, polypropylene, poly-1-butene, poly-4-methyl-1-pentene, an ethylene/propylene copolymer, an ethylene/1-butene copolymer, an ethylene/vinyl acetate copolymer, an ethylene/ethyl acrylate copolymer, and an ethylene/vinyl alcohol copolymer, polyester-based resins such as polyethylene terephthalate, polyethylene naphthalate, and polybutylene terephthalate, polyamide-based resins such as polyacrylate, polystyrene, nylon 6, nylon 6,6, and partially aromatic polyamide, polyvinyl chloride-based resins, polyvinylidene chloride-based resins, polycarbonate resins, and the like, and a mixture thereof. The base material layer may be made as a monolayer or a laminate of two or more layers. Further, base material film may be subjected to a surface treatment such as a corona discharge treatment, a plasma treatment, a chromic acid treatment, sandblast, and a solvent treatment for the purpose of improving the adhesion with the strippable layer.

The thickness of the base material layer and the strippable layer can be suitably selected according to the uses.

The tape of the present embodiment having the configuration can be used specifically for substrate polishing, a plating method, or the like.

The method for polishing a substrate using the tape of the present embodiment specifically has a step of attaching the tape onto the backside of the surface to be polished in a substrate through the strippable layer, a step of polishing the surface to be polished in the substrate, and a step of applying heat to the strippable layer of the tape after polishing step to strip the tape from the backside.

Examples of the substrate include a silicon wafer, a sapphire substrate, and a metallic substrate.

In the step of polishing the surface to be polished, methods known in the related art can be carried out using polishing particles, diamond wheels, or the like. Further, by applying heat in the above-described temperature range to strip the tape from the backside of the surface to be polished in the substrate.

In The method for polishing the substrate of the present embodiment, a tape provided with a strippable layer including the above-described adhesive resin composition is used, and the backside of the substrate is ensured to be protected during the back-grinding step, and thus, the tape stripping step can be carried out by a simple method, heating. Further, the stress to the substrate during the stripping is inhibited, and thus, even in an ultra-thin substrate, the warp of the substrate is reduced. Further, the contamination of the substrate in the stripping step is reduced, and thus, the yield of the product is enhanced.

The plating method using the tape of the present embodiment specifically has a step of attaching the tape to a place to be not plated in a body to be plated, a step of subjecting the body to be plated to a plating treatment, and a step of stripping the tape by applying heat to the strippable layer of the tape attached to the body to be plated after the plating treatment step.

Examples of the body to be plated include metallic substrates, and the plating method may be carried out by a known method.

In the plating method of the present embodiment, a tape provided with a strippable layer including the above-described adhesive resin composition is used, and the backside of the substrate is ensured to be protected during the plating the place to be not plated in the body to be plated, and thus, the tape stripping step can be carried out by a simple method, heating. Further, the contamination of the substrate during the stripping step is reduced, and thus, the yield of the product is enhanced.

Furthermore, the tape in the present embodiment can be applied to an assembly tape for QFN (Quad Flat Non-Leaded Package), or the like.

As described above, Embodiment 1 of the present invention has been described with reference to the drawings, but these are illustrative of the present invention, and various other configurations can be employed.

Embodiment 2

Adhesive Resin Composition

The adhesive resin composition of the present embodiment includes a Meldrum's acid derivative represented by the general formula (1) and an adhesive resin.

(Meldrum's Acid Derivative)

In the present embodiment, as the Meldrum's acid derivative, the same Meldrum's acid derivative as in Embodiment 1 can be used.

Further, in the present embodiment, at least one of $R^1$, $R^2$, $R^3$, $R^4$, the ring structures formed by the mutual bonding of $R^1$ and $R^2$, and the ring structures formed by the mutual bonding of $R^3$ and $R^4$ may have a reactive functional group as a substituent as exemplified in Embodiment 1.

As the Meldrum's acid derivative used in the present embodiment, ones having a structure capable of generating a carbon dioxide gas or the like can be used. Specific examples thereof include the following.

1. The Meldrum's acid derivative, in which $R^3$ and $R^4$ are both methyl groups.
2. The Meldrum's acid derivative, in which $R^3$ is a methyl group and $R^4$ is an ethyl group.
3. The Meldrum's acid derivative, in which $R^3$ and $R^4$ are both ethyl groups.
4. The Meldrum's acid derivative having a cyclopentyl group formed by the mutual bonding of $R^3$ and $R^4$.
1. The Meldrum's acid derivative, in which $R^3$ and $R^4$ are both methyl groups.

Examples of the Meldrum's acid derivative include 2,2-dimethyl-1,3-dioxane-4,6-dione, 2,2,5-trimethyl-1,3-dioxane-4,6-dione, 5-ethyl-2,2-dimethyl-1,3-dioxane-4,6-dione, 5-benzyl-2,2-dimethyl-1,3-dioxane-4,6-dione, 5-phenyl-2,2-dimethyl-1,3-dioxane-4,6-dione, 2,2,5,5-tetramethyl-1,3-dioxane-4,6-dione, 5-ethyl-2,2,5-trimethyl-1,3-dioxane-4,6-dione, 5-benzyl-2,2,5-trimethyl-1,3-dioxane-4,6-dione, 5-phenyl-2,2,5-trimethyl-1,3-dioxane-4,6-dione, 5,5-diethyl-2,2-dimethyl-1,3-dioxane-4,6-dione, 5-benzyl-5-ethyl-2,2-dimethyl-1,3-dioxane-4,6-dione, 5-phenyl-5-ethyl-2,2-dimethyl-1,3-dioxane-4,6-dione, 5,5-dibenzyl-2,2-dimethyl-1,3-dioxane-4,6-dione, and 5-phenyl-5-benzyl-2,2-dimethyl-1,3-dioxane-4,6-dione.

2. The Meldrum's acid derivative, in which $R^3$ is a methyl group and $R^4$ is an ethyl group.

Examples of the Meldrum's acid derivative include 2-ethyl-2-methyl-1,3-dioxane-4,6-dione, 2-ethyl-2,5-dimethyl-1,3-dioxane-4,6-dione, 2,5-diethyl-2-methyl-1,3-dioxane-4,6-dione, 5-benzyl-2-ethyl-2-methyl-1,3-dioxane-4,6-dione, 5-phenyl-2-ethyl-2-methyl-1,3-dioxane-4,6-dione, 2-ethyl-2,5,5-trimethyl-1,3-dioxane-4,6-dione, 2,5-diethyl-2,5-dimethyl-1,3-dioxane-4,6-dione, 5-benzyl-2-ethyl-2,5-dimethyl-1,3-dioxane-4,6-dione, 2-ethyl-5-phenyl-2,5-dimethyl-1,3-dioxane-4,6-dione, 2,5,5-triethyl-2-methyl-1,3-dioxane-4,6-dione, 5-benzyl-2,5-diethyl-2-methyl-1,3-dioxane-4,6-dione, 5-phenyl-2,5-diethyl-2-methyl-1,3-dioxane-4,6-dione, 5,5-dibenzyl-5-ethyl-2-dimethyl-1,3-dioxane-4,6-dione, 5-phenyl-5-benzyl-2-ethyl-2-methyl-1,3-dioxane-4,6-dione, and 5-(p-styrylmethyl)-2-ethyl-2,5-dimethyl-1,3-dioxane-4,6-dione.

3. The Meldrum's acid derivative, in which $R^3$ and $R^4$ are both ethyl groups.

Examples of the Meldrum's acid derivative include 2,2-diethyl-1,3-dioxane-4,6-dione, 5-methyl-2,2-diethyl-1,3-dioxane-4,6-dione, 2,2,5-triethyl-1,3-dioxane-4,6-dione, 5-benzyl-2,2-diethyl-1,3-dioxane-4,6-dione, 5-phenyl-2,2-diethyl-1,3-dioxane-4,6-dione, 5,5-dimethyl-2,2-diethyl-1,3-dioxane-4,6-dione, 5-methyl-2,2,5-triethyl-1,3-dioxane-4,6-dione, 5-benzyl-5-methyl-2,2-diethyl-1,3-dioxane-4,6-dione, 5-phenyl-5-methyl-2,2-diethyl-1,3-dioxane-4,6-dione, 2,2,5,5-tetraethyl-1,3-dioxane-4,6-dione, 5-benzyl-2,2,5-triethyl-1,3-dioxane-4,6-dione, 5-phenyl-2,2,5-triethyl-1,3-dioxane-4,6-dione, 5,5-dibenzyl-2,2-diethyl-1,3-dioxane-4,6-dione, 5-phenyl-5-benzyl-2,2-diethyl-1,3-dioxane-4,6-dione, and 5-(p-styrylmethyl)-2,2-diethyl-5-methyl-1,3-dioxane-4,6-dione.

4. The Meldrum's acid derivative having a cyclopentyl group formed by the mutual bonding of $R^3$ and $R^4$.

Examples of the Meldrum's acid derivative include spiro-[4,5]-6,10-dioxadecane-7,9-dione, 8-methyl-spiro-[4,5]-6,10-dioxadecane-7,9-dione, 8-ethyl-spiro-[4,5]-6,10-dioxadecane-7,9-dione, 8-benzyl-spiro-[4,5]-6,10-dioxadecane-7,9-dione, 8-phenyl-spiro-[4,5]-6,10-dioxadecane-7,9-dione, 8,8-dimethyl-spiro-[4,5]-6,10-dioxadecane-7,9-dione, 8-ethyl-8-methyl-spiro-[4,5]-6,10-dioxadecane-7,9-dione, 8-benzyl-8-methyl-spiro-[4,5]-6,10-dioxadecane-7,9-dione, 8-phenyl-8-methyl-spiro-[4,5]-6,10-dioxadecane-7,9-dione, 8,8-diethyl-spiro-[4,5]-6,10-dioxadecane-7,9-dione, 8-benzyl-8-ethyl-spiro-[4,5]-6,10-dioxadecane-7,9-dione, 8-phenyl-8-ethyl-spiro-[4,5]-6,10-dioxadecane-7,9-dione, 8,8-dibenzyl-spiro-[4,5]-6,10-dioxadecane-7,9-dione, 8-benzyl-8-phenyl-spiro-[4,5]-6,10-dioxadecane-7,9-dione, and 8-(p-styrylmethyl)-8-methyl-6,10-dioxaspiro[4,5]decane-7,9-dione.

In the present embodiment, among those described above, 2-ethyl-2,5-dimethyl-1,3-dioxane-4,6-dione, 8-methyl-6,10-dioxaspiro[4,5]decane-7,9-dione, 2,2,5,5-tetramethyl-1,3-dioxane-4,6-dione, 5-benzyl-2,2,5-trimethyl-1,3-dioxane-4,6-dione, 2-ethyl-2,5,5-trimethyl-1,3-dioxane-4,6-dione, 8,8-dimethyl-6,10-dioxaspiro[4,5]decane-7,9-dione, 5-benzyl-2-ethyl-2,5-dimethyl-1,3-dioxane-4,6-dione, and 8-benzyl-8-methyl-6,10-dioxaspiro[4,5]decane-7,9-dione are preferably used.

(Adhesive Resin)

As the adhesive resin, ones maintaining the adhesiveness at lower than the heating temperature during the stripping, and having heat resistance not generating melting, decomposition, or the like can be used. The adhesive resin has a glass transition temperature measured by differential scanning calorimetry (DSC) of equal to or lower than 40° C., and preferably equal to or lower than 30° C., and has adhesiveness at ambient temperature. For example, sticky substance such as a pressure sensitive adhesive (sticky material), known in the related art, can be used.

Examples of the pressure sensitive adhesive include rubber-based pressure sensitive adhesives using rubber-based polymers such as natural rubber or polyisobutylene rubber, styrene/butadiene rubber, styrene/isoprene/styrene block copolymer rubber, reclaimed rubber, butyl rubber, polyisobutylene rubber, and NBR as a base polymer; silicone-based pressure sensitive adhesives; urethane-based pressure sensitive adhesives; and acryl-based pressure sensitive adhesives. The base material can be constituted with one kind or two or more kinds of components. An acryl-based pressure sensitive adhesive is particularly preferred.

Examples of the acryl-based pressure sensitive adhesive include acryl-based sticky materials having one kind or two or more kinds of acryl-based polymer (homopolymer or copolymer) using an alkyl (meth)acrylate ester as a monomer component as a base polymer. Examples of the alkyl (meth)acrylate ester in the acryl-based pressure sensitive adhesive include $C_{1-20}$ alkyl (meth)acrylate esters such as methyl (meth)acrylate, ethyl (meth)acrylate, propyl (meth)acrylate, isopropyl (meth)acrylate, butyl (meth)acrylate, isobutyl (meth)acrylate, s-butyl (meth)acrylate, t-butyl (meth)acrylate, pentyl (meth)acrylate, hexyl (meth)acrylate, heptyl (meth)acrylate, octyl (meth)acrylate, 2-ethylhexyl (meth)acrylate, isooctyl (meth)acrylate, nonyl (meth)acrylate, isononyl (meth)acrylate, decyl (meth)acrylate, isodecyl (meth)acrylate, undecyl (meth)acrylate, dodecyl (meth)acrylate, tridecyl (meth)acrylate, tetradecyl (meth)acrylate, pentadecyl (meth)acrylate, hexadecyl (meth)acrylate, heptadecyl (meth)acrylate, octadecyl (meth)acrylate, nonadecyl (meth)acrylate, and eicosyl (meth)acrylate, and preferably $C_{4-18}$ alkyl (meth)acrylates (linear or branched alkyl) esters.

Furthermore, the acryl-based pressure sensitive adhesive may include units corresponding to other monomer components which can be copolymerizable with the alkyl (meth)acrylate esters, for the purpose of improving aggregation power, heat resistance, crosslinkability, or the like, if necessary. Examples of the monomer component include carboxyl group-containing monomers such as acrylic acid, methacrylic acid, carboxyethyl acrylate, carboxypentyl acrylate, itaconic acid, maleic acid, fumaric acid, and crotonic acid; acid anhydride group-containing monomers such as maleic anhydride, and itaconic anhydride; hydroxyl group-containing monomers such as hydroxyethyl (meth)acrylate, hydroxypropyl (meth)acrylate, hydroxybutyl (meth)acrylate, hydroxyhexyl (meth)acrylate, hydroxyoctyl (meth)acrylate, hydroxydecyl (meth)acrylate, hydroxylauryl (meth)acrylate, and (4-hydroxymethylcyclohexyl)methyl-methacrylate; sulfonic acid group-containing monomers such as styrenesulfonic acid, allylsulfonic acid, 2-(meth)acrylamide-2-methylpropanesulfonic acid, (meth)acrylamide propanesulfonic acid, sulfopropyl (meth)acrylate, and (meth)acryloyl oxynaphthalenesulfonic acid; phosphoric acid group-containing monomers such as 2-hydroxyethyl-acryloyl phosphate; (N-substituted)amide-based monomers such as (meth)acryl amide, N,N-dimethyl (meth)acrylamide, N,N-diethyl (meth)acrylamide, N-isopropyl (meth)acrylamide, N-butyl (meth)acrylamide, N-methylol (meth)acrylamide, and N-methylolpropane (meth)acrylamide; aminoalkyl (meth)acrylate-based monomers such as aminoethyl (meth)acrylate, N,N-dimethylaminoethyl (meth)acrylate, and t-butylaminoethyl (meth)acrylate; alkoxyalkyl (meth)acrylate-based monomers such as methoxyethyl (meth)acrylate and ethoxyethyl (meth)acrylate; maleimide-based monomers such as N-cyclohexylmaleimide, N-isopropylmaleimide, N-laurylmaleimide, and N-phenylmaleimide; itaconimide-based monomers such as N-methylitaconimide, N-ethylitaconimide, N-butylitaconimide, N-octylitaconimide, N-2-ethylhexylitaconimide, N-cyclohexylitaconimide, and N-laurylitaconimide; succinimide-based monomers such as N-(meth)acryloyloxymethylene succinimide, N-(meth)acryloyl-6-oxyhexamethylene succinimide, and N-(meth)acryloyl-8-oxyoctamethylene succinimide; vinylesters such as vinyl acetate and vinyl propionate; nitrogen-containing heterocyclic ring-based monomers such as N-vinyl-2-pyrrolidone, N-methylvinylpyrrolidone, N-vinylpyridine, N-vinylpiperidone, N-vinylpyrimidine, N-vinylpiperazine, N-vinylpyrazine, N-vinylpyrrole, N-vinylimidazole, N-vinyloxazole, N-(meth)acryloyl-2-pyrrolidone, N-(meth)acryloylpiperidine, N-(meth)acryloylpyrrolidine, and N-vinylmorpholine; N-vinylcarboxylic acid amides; styrene-based monomers such as styrene and α-methylstyrene; lactam-based monomers such as N-vinylcaprolactam; cyanoacrylate monomers such as acrylonitrile and methacrylonitrile; epoxy group-containing acryl-based monomers such as glycidyl (meth)acrylate; glycol-based acryl ester monomers such as polyethylene glycol (meth)acrylate, polypropylene glycol (meth)acrylate, methoxyethylene glycol (meth)acrylate, and methoxypolypropylene glycol (meth)acrylate; acrylate ester-based monomers having a heterocyclic ring, a halogen atom, a silicon atom, or the like, such as tetrahydrofurfuryl (meth)acrylate, fluorine (meth)acrylate, and silicone (meth)acrylate; polyfunctional monomers such as hexanediol di(meth)acrylate, (poly)ethylene glycol di(meth)acrylate, (poly)propylene glycol di(meth)acrylate, neopentyl glycol di(meth)acrylate, pentaerythritol di(meth)acrylate, trimethylolpropane tri(meth)acrylate, pentaerythritol tri(meth)acrylate, dipentaerythritol hexa(meth)acrylate, epoxyacrylate, polyesteracrylate, urethane acrylate, divinylbenzene, butyl di(meth)acrylate, and hexyl di(meth)acrylate; olefin-based monomers such as isoprene, butadiene, and isobutylene; and vinyl ether-based monomers such as methyl vinyl ether and ethyl vinyl ether. These monomer components may be used alone or in combination of two or more kinds thereof.

The preparation of the acryl-based pressure sensitive adhesive may be any one suitably selected from known preparation methods such as solution polymerization, bulk polymerization, emulsion polymerization, and various kinds of radical polymerization. In addition, the obtained adhesive resin may be any one of a random copolymer, a block copolymer, and a graft copolymer.

Furthermore, in the solution polymerization out of the radical polymerization, for example, ethyl acetate, toluene, or the like is used as a polymerization solvent. As a specific example of the solution polymerization, for example, 0.01 parts by weight to 0.2 parts by weight of azobisisobutyronitrile with respect to 100 parts by weight of the total amount of the monomers is added as a polymerization initiator, under an inert gas flow such as nitrogen, and the reaction is carried out usually at about 50° C. to 100° C. for about 8 hours to 30 hours.

The polymerization initiator, the chain transfer agent, the emulsifier, and the like used in the radical polymerization are not particularly limited, and any one can be suitably selected and used.

Examples of the polymerization initiator include azo initiators such as 2,2'-azobisisobutyronitrile, 2,2'-azobis(2-amidinopropane)dihydrochloride, 2,2'-azobis[2-(5-methyl-2-imidazolin-2-yl)propane]dihydrochlorid e, 2,2'-azobis(2-methylpropionamidine)disulfate, 2,2'-azobis(N,N'-dimethyleneisobutylamidine), and 2,2'-azobis[N-(2-carboxyethyl)-2-methylpropionamidine]hydrate (VA-057, manufactured by Wako Pure Chemical Industries, Ltd.), other persulfates such as potassium persulfate and ammonium persulfate, peroxide initiators such as di(2-ethylhexyl) peroxydicarbonate, di(4-t-butylcyclohexyl)peroxydicarbonate, di-sec-butyl peroxydicarbonate, t-butyl peroxyneodecanoate, t-hexyl peroxypivalate, t-butyl peroxypivalate, dilauroyl peroxide, di-n-octanoyl peroxide, 1,1,3,3-tetramethylbutylperoxy-2-ethyl hexanoate, di(4-methylbenzoyl) peroxide, dibenzoyl peroxide, t-butyl peroxy isobutylate, 1,1-di(t-hexylperoxy)cyclohexane, t-butyl hydroperoxide and hydrogen peroxide, and redox initiators formed by combination of peroxide and a reducing agent, such as a combination of persulfate and sodium hydrogen sulfite, and a combination of peroxide and sodium ascorbate, but are not limited to these examples.

Furthermore, in the case where an organic peroxide is used as a polymerization initiator, it is possible to use the residual organic peroxide, which is not used in a polymerization reaction, in a crosslinking reaction. However, in this case, the residual amount may be determined and then added again, if necessary, and a predetermined amount of the organic peroxide can be used.

The polymerization initiator may be used alone or as a mixture of two or more kinds thereof, and the total content by volume is preferably about 0.005 parts by weight to 1 part by weight, and more preferably about 0.02 parts by weight to 0.6 parts by weight, with respect to 100 parts by weight of the monomers.

Moreover, a chain transfer agent may be used in polymerization. By using the chain transfer agent, the molecular weight of the adhesive resin can be adjusted appropriately.

Examples of the chain transfer agent include lauryl mercaptan, glycidyl mercaptan, mercaptoacetic acid, 2-mercaptoethanol, thioglycolic acid, 2-ethylhexyl thioglycolate, and 2,3-dimercapto-1-propanol.

These chain transfer agents may be used alone or as a mixture of two or more kinds thereof, and the total content by volume is about 0.01 parts by weight to 0.4 parts by weight with respect to 100 parts by weight of the monomers.

In addition, examples of the emulsifier used in the case of the emulsion polymerization include anionic emulsifiers such as sodium lauryl sulfate, ammonium lauryl sulfate, sodium dodecyl benzene sulfonate, ammonium polyoxyethylene alkyl ether sulfate, and sodium polyoxyethylene alkyl phenyl ether sulfate, and nonionic emulsifiers such as polyoxyethylene alkyl ether, polyoxyethylene alkyl phenyl ether, polyoxyethylene fatty acid ester, and a polyoxyethylene-polyoxypropylene block polymer. These emulsifiers may be used alone or as a mixture of two or more kinds thereof.

Moreover, specific examples of the emulsifiers introducing radical polymerizable functional groups such as a propenyl group and an allyl ether group, as a reactive emulsifier, include Aqualon HS-10, HS-20, KH-10, BC-05, BC-10, and BC-20 (manufactured by Dai-ichi Kogyo Seiyaku Co., Ltd.), and Adekaria Soap SE10N (manufactured by ADEKA Corporation). Since the reactive emulsifier is taken into the polymer chain after polymerization, water resistance is improved, which is thus preferable. The amount of the emulsifier to be used is 0.3 parts by weight to 5 parts by weight with respect to 100 parts by weight of the monomers, and more preferably 0.5 parts by weight to 1 part by weight, from the viewpoints of polymerization stability or mechanical stability.

The crosslinking reaction of the adhesive resin itself proceeds by heating during the stripping, and thus, an adhesive resin having reduced adhesion performance can be used. In this case, it is necessary to consider that the adhesion is not reduced at lower than the temperature during the stripping.

(Other Components)

In the adhesive resin composition of the present embodiment, as the other components, the same components as in Embodiment 1 can be used.

(Method for Preparing Adhesive Resin Composition)

The adhesive resin composition is obtained by mixing the adhesive resin as described above and other components depending on the uses with the Meldrum's acid derivative by a method in the related art. As the mixing method, mixing using stirring in a tank, mixing by a kneader, or the like can be used.

(Adhesive Resin Composition)

In the adhesive resin composition obtained by the above-described preparation method, the Meldrum's acid derivative can be included in the amount of 0.1 parts by weight to 50 parts by weight, preferably 0.5 parts by weight to 40 parts by weight, and more preferably 1 part by weight to 30 parts by weight, with respect to 100 parts by weight of the adhesive resin. If the addition amount of the expanding agent (Meldrum's acid derivative) is less than the ranges, the amount of the carbon dioxide gas generated is low and the effect of the expanding agent is hardly obtained, and as a result, the stripping effect is low. On the other hand, if the addition amount of the expanding agent is more than the ranges, it causes a part of the strippable layer to remain in the adherend after stripping the adherend, which is a so-called "adhesive residue". That is, if the Meldrum's acid derivative is included in the ranges, the stripping effect is excellent, and thus, an adhesive resin composition having inhibited adhesive residues can be obtained.

<Laminate, Self-Stripping Method, and Uses>

The laminate 10 of the present embodiment shown in FIG. 1 has the same structure as in Embodiment 1 except that the strippable layer 14 including the adhesive resin composition of the present embodiment is used.

The self-stripping method of the present embodiment can be carried out in the same manner as in Embodiment 1 except that the above-described laminate 10 is used.

The adhesive resin composition of the present embodiment or the laminate 10 can be applied in the same uses as in Embodiment 1.

As described above, Embodiment 2 of the present invention has been described with reference to the drawings, but these are illustrative of the present invention, and various other configurations can be employed.

EXAMPLES

Hereinafter, the present invention will be described in more detail with reference to Examples 1 and 2, but the range of the present invention is not limited to these Examples or the like.

Example 1

Preparation Example A1

100 g of methylmalonic acid (manufactured by Tokyo Chemical Industry Co., Ltd.) and 100 g of acetic anhydride were charged into a 500-mL 4-necked flask. 0.5 g of 98% sulfuric acid was subsequently charged to the flask, and then 75 g of methylethylketone was added dropwise thereto over 1 hour with a dropping funnel. After stirring at room temperature for 24 hours, 200 g of ethyl acetate and 300 g of distilled water were added thereto to carry out extraction of the organic layer with a separating funnel. The solvent was evaporated from the obtained organic layer with an evaporator to obtain 75 g of 2-ethyl-2,5-dimethyl-1,3-dioxane-4,6-dione. $H^1$ NMR (300 MHz) was measured and the following peaks were obtained. δ=1.04-1.12 (m, 3H), 1.57-1.61 (m, 3H), 1.71 (s, 1.12H), 1.77 (s, 1.92H), 1.95-2.16 (m, 2H), 3.53-5.65 (m, 1H)

Preparation Example A2

The same procedure as in Preparation Example A1 except that 75 g of methylethylketone in Preparation Example A1 was changed to 80 g of cyclopentanone was carried out to obtain 80 g of 8-methyl-6,10-dioxaspiro[4,5]decane-7,9-dione. $H^1$ NMR (300 MHz) was measured and the following peaks were obtained. δ=1.53 (d, 5.4 Hz, 3H), 1.84-1.97 (m, 4H), 2.21-2.27 (m, 4H), 3.63 (q, 5.4 Hz, 1H)

Preparation Example A3

100 g of 2,2,5-trimethyl-1,3-dioxane-4,6-dione (manufactured by Tokyo Chemical Industry Co., Ltd.) and 100 g of dimethyl formamide were charged into a 500-mL 4-necked flask. 95 g of potassium carbonate was subsequently charged to the flask, and then 97 g of 4-chloromethylstyrene was added dropwise thereto over 1 hour with a dropping funnel. After stirring at 40° C. for 24 hours, 400 g of ethyl acetate was added thereto and the solid produced was separated by filtration by Nutsche. Washing was carried out twice with a separating funnel using 300 mL of distilled water. The solvent was evaporated with an evaporator to obtain 150 g of 5-(p-styrylmethyl)-2,2,5-trimethyl-1,3-dioxane-4,6-dione. $H^1$ NMR (300 MHz) was measured and the following peaks were obtained. δ=0.97 (s, 3H), 1.60 (s, 3H), 1.75 (s, 3H), 3.31 (s, 2H), 5.22 (d, 12.0 Hz, 1H), 5.70 (d, 19.5 Hz, 1H), 6.65 (dd, 12.0, 19.5 Hz, 1H), 7.13 (d, 9.0 Hz, 2H), 7.31 (d, 9.0 Hz, 2H)

Preparation Example A4

The same procedure as in Preparation Example A3 except that 100 g of 2,2,5-trimethyl-1,3-dioxane-4,6-dione was changed to 92 g of 2-ethyl-2,5-dimethyl-1,3-dioxane-4,6-dione synthesized in Preparation Example A1 was carried out to obtain 132 g of 5-(p-styrylmethyl)-2-ethyl-2,5-dimethyl-1,3-dioxane-4,6-dione. $H^1$ NMR (300 MHz) was measured and the following peaks were obtained. δ=0.43 (t, 8.1 Hz, 1.6H), 0.83 (s, 1.3H), 0.94 (t, 8.1 Hz, 1.4H), 1.27 (q, 8.1 Hz, 1.2H), 1.57 (s, 1.7H), 1.75 (s, 3H), 1.80 (q, 8.1 Hz, 0.8H), 3.31 (s, 2H), 5.22 (d, 12.0 Hz, 1H), 5.70 (d, 19.5 Hz, 1H), 6.65 (dd, 12.0, 19.5 Hz, 1H), 7.16 (d, 9.0 Hz, 2H), 7.31 (d, 9.0 Hz, 2H)

Preparation Example A5

The same procedure as in Preparation Example A3 except that 100 g of 2,2,5-trimethyl-1,3-dioxane-4,6-dione was changed to 85 g of 8-methyl-6,10-dioxaspiro[4,5]decane-7,9-dione synthesized in Preparation Example A2 was carried out to obtain 125 g of 8-(p-styrylmethyl)-8-methyl-6,10-dioxaspiro[4,5]decane-7,9-dione. $H^1$ NMR (300 MHz) was measured and the following peaks were obtained. δ=1.28-1.38 (m, 2H), 1.56-1.82 (m, 4H), 1.74 (s, 3H), 2.00-2.05 (m, 2H), 3.32 (s, 2H), 5.22 (d, 12.0 Hz, 1H), 5.70 (d, 12.0 Hz, 1H), 6.66 (dd, 12.0, 19.5 Hz, 1H), 7.13 (d, 9.0 Hz, 2H), 7.31 (d, 9.0 Hz, 2H)

Preparation Example A6

The same procedure as in Preparation Example A1 except that 75 g of methylethylketone in Preparation Example A1 was changed to 80 g of diethylketone was carried out to obtain 80 g of 2,2-diethyl-5-methyl-1,3-dioxane-4,6-dione. $H^1$ NMR (300 MHz) was measured and the following peaks were obtained. δ=1.04 (q, 8.1 Hz, 6H), 1.58 (d, 7.8 Hz, 3H), 1.96 (s, 8.1 Hz, 2H), 2.05 (s, 8.1 Hz, 2H), 3.57 (q, 5.4 Hz, 1H)

Preparation Example A7

The same procedure as in Preparation Example A3 except that 100 g of 2,2,5-trimethyl-1,3-dioxane-4,6-dione was changed to 85 g of 2,2-diethyl-5-methyl-1,3-dioxane-4,6-dione synthesized in Preparation Example A1 was carried out to obtain 132 g of 5-(p-styrylmethyl)-2,2-diethyl-5-methyl-1,3-dioxane-4,6-dione. $H^1$ NMR (300 MHz) was measured and the following peaks were obtained. δ=0.40 (t, 8.1 Hz, 3H), 0.94 (t, 8.1 Hz, 3H), 1.14 (q, 8.1 Hz, 2H), 1.70 (s, 3H), 1.80 (q, 8.1 Hz, 2H), 3.31 (s, 2H), 5.22 (d, 12.0 Hz, 1H), 5.70 (d, 19.5 Hz, 1H), 6.65 (dd, 12.0, 19.5 Hz, 1H), 7.13 (d, 9.0 Hz, 2H), 7.30 (d, 9.0 Hz, 2H)

Preparation Example A8

20 g of butyl acrylate, 55 g of 2-ethylhexyl acrylate, 15 g of methyl methacrylate, 10 g of hydroxyethyl methacrylate, and 100 g of ethyl acetate were added to a 500-mL 4-necked flask, and mixed at room temperature. Further, 0.2 g of 2,2'-azobisvaleronitrile was added thereto, and the mixture was heated to 75° C. and then kept to be stirred for 10 hours. 0.1 g of dibutyl tin dilaurate and 5 g of 2-isocyanatoethyl methacrylate were added thereto and the mixture was stirred at 75° C. for additional 10 hours to obtain an acryl-based sticky material L having a molecular weight of 300,000. The glass transition temperature was measured by differential scanning calorimetry (DSC-60, manufactured by Shimadzu Corporation) and found to be −40° C.

Example A1

15 g of 5-(p-styrylmethyl)-2,2,5-trimethyl-1,3-dioxane-4,6-dione synthesized in Preparation Example A3, 20 g of butyl acrylate, 63 g of 2-ethylhexyl acrylate, 2 g of methacrylic acid, and 100 g of ethyl acetate were added to a 500-mL 4-necked flask, and mixed at room temperature. Further, 0.2 g of 2,2'-azobisvaleronitrile was added thereto, and the mixture was heated to 75° C. and then kept to be stirred for 10 hours to obtain an acryl-based sticky material A having a molecular weight of 300,000. The glass transition temperature was measured by differential scanning calorimetry (DSC-60, manufactured by Shimadzu Corporation) and found to be 14° C.

100 parts by weight of the obtained acryl-based sticky material A, 2 parts by weight of an epoxy compound (TETRAD-C, manufactured by Mitsubishi Gas Chemical Company, Inc.), and 50 parts by weight of ethyl acetate were added thereto to afford a sticky material composition (adhesive resin composition).

The obtained sticky material composition was coated onto PET having a release-treated surface to a thickness of a dried film of 20 µm using an applicator, and then heated at 120° C. for 5 minutes, and the coating solution was dried. Then, the residue was attached to the PET film and cured at 60° C. for 1 day to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes, and immediately after taking out from the hot plate, the tape was stripped to confirm the strippability and the adhesive residues according to the following criteria. The results are shown in Table 1.

(Strippability)

After the tape was vacuum-chucked, the tape was lift vertically to carry out the stripping. A case of being stripped was indicated as o and a case of being not stripped was indicated as x.

(Adhesive Residue)

After the stripping, the SUS plate was visually observed and determined. A case where even a little adhesive residue was recognized was indicated as x.

Example A2

The same procedure as in Example A1 except that 15 g of 5-(p-styrylmethyl)-2,2,5-trimethyl-1,3-dioxane-4,6-dione was changed to 5-(p-styrylmethyl)-2-ethyl-2,5-dimethyl-1,3-dioxane-4,6-dione synthesized in Preparation Example A4 was carried out to obtain an acryl-based sticky material B having a molecular weight of 300,000. The glass transition temperature was measured by differential scanning calorimetry (DSC-60, manufactured by Shimadzu Corporation) and found to be 13° C.

100 parts by weight of the obtained acryl-based sticky material B, 2 parts by weight of an epoxy compound (TETRAD-C, manufactured by Mitsubishi Gas Chemical Company, Inc.), and 50 parts by weight of ethyl acetate were added thereto to afford a sticky material composition.

The obtained sticky material composition was coated onto PET having a release-treated surface to a thickness of a dried film of 20 µm using an applicator, and then heated at 120° C. for 5 minutes, and the coating solution was dried. Then, the residue was attached to the PET film and cured at 60° C. for 1 day to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes to confirm the expandability. After taking out from the hot plate, the tape was stripped to confirm the strippability and the adhesive residues. The results are shown in Table 1.

Example A3

The same procedure as in Example A1 except that 15 g of 5-(p-styrylmethyl)-2,2,5-trimethyl-1,3-dioxane-4,6-dione was changed to 8-(p-styrylmethyl)-8-methyl-6,10-dioxaspiro[4,5]decane-7,9-dione synthesized in Preparation Example A5 was carried out to obtain an acryl-based sticky material C having a molecular weight of 300,000. The glass transition temperature was measured by differential scanning calorimetry (DSC-60, manufactured by Shimadzu Corporation) and found to be 11° C.

100 parts by weight of the obtained acryl-based sticky material C, 2 parts by weight of an epoxy compound (TETRAD-C, manufactured by Mitsubishi Gas Chemical Company, Inc.), and 50 parts by weight of ethyl acetate were added thereto to afford a sticky material composition. The obtained sticky material composition was coated onto PET having a release-treated surface to a thickness of a dried film of 20 μm using an applicator, and then heated at 120° C. for 5 minutes, and the coating solution was dried. Then, the residue was attached to the PET film and cured at 60° C. for 1 day to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes to confirm the expandability. After taking out from the hot plate, the tape was stripped to confirm the strippability and the adhesive residues. The results are shown in Table 1.

Comparative Example A1

80 g of butyl acrylate, 15 g of ethyl acrylate, 5 g of methacrylic acid, and 100 g of ethyl acetate were added to a 500-mL 4-necked flask, and mixed at room temperature. Further, 0.2 g of 2,2'-azobisvaleronitrile was added thereto, and the mixture was heated to 75° C. and then kept to be stirred for 10 hours to obtain an acryl-based sticky material D having a molecular weight of 400,000. The glass transition temperature was measured by differential scanning calorimetry (DSC-60, manufactured by Shimadzu Corporation) and found to be −40° C.

100 parts by weight of the obtained acryl-based sticky material D, 2 parts by weight of an epoxy compound (TETRAD-C, manufactured by Mitsubishi Gas Chemical Company, Inc.), 25 parts by weight of 2,2'-azobis-(N-butyl-2-methylpropionamide), and 50 parts by weight of ethyl acetate were added thereto to afford a sticky material composition. The obtained sticky material composition was coated onto PET having a release-treated surface to a thickness of a dried film of 20 μm using an applicator, and then heated at 100° C. for 2 minutes, and the coating solution was dried. Then, the residue was attached to the PET film and cured at 40° C. for 3 days to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes, and immediately after taking out from the hot plate, the tape was stripped to confirm the strippability and the adhesive residues according to the following criteria. The results are shown in Table 1.

Comparative Example A2

100 parts by weight of the acryl-based sticky material D obtained in Comparative Example A1, 2 parts by weight of an epoxy compound (TETRAD-C, manufactured by Mitsubishi Gas Chemical Company, Inc.), 25 parts by weight of Matsumoto Microsphere FN-180 (thermally expandable microcapsule, manufactured by Matsumoto Yushi-Seiyaku Co., Ltd.), and 50 parts by weight of ethyl acetate were added to afford a sticky material composition. The obtained sticky material composition was coated onto PET having a release-treated surface to a thickness of a dried film of 20 μm using an applicator, and then heated at 100° C. for 2 minutes, and the coating solution was dried. Then, the residue was attached to the PET film and cured at 40° C. for 3 days to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes, and immediately after taking out from the hot plate, the tape was stripped. The strippability and the adhesive residues were confirmed. The results are shown in Table 1.

TABLE 1

|  | Strippability | Adhesive residue |
| --- | --- | --- |
| Example A1 | ○ | ○ |
| Example A2 | ○ | ○ |
| Example A3 | ○ | ○ |
| Comparative Example A1 | ○ | x |
| Comparative Example A2 | ○ | x |

Example A4

100 parts by weight of the acryl-based sticky material A obtained in Example A1, 2 parts by weight of an epoxy compound (TETRAD-C, manufactured by Mitsubishi Gas Chemical Company, Inc.), and 50 parts by weight of ethyl acetate were added to afford a sticky material composition. The obtained sticky material composition was coated onto PET having a release-treated surface to a thickness of a dried film of 20 μm using an applicator, and then heated at 120° C. for 5 minutes, and the coating solution was dried. Then, the residue was attached to the PET film and cured at 60° C. for 1 day to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes, and immediately after taking out from the hot plate, the tape was stripped. For the evaluation of contamination properties, Electron Spectroscopy for Chemical Analysis (ESCA) measurement (measurement instrument: ESCALAB200iXL manufactured by VG Scientific, Ltd., X-ray source: AlKα, analysis area: φ150 μm) was carried out to measure the amount of carbon present on the surface of the silicon wafer. Further, for the evaluation, the ratio of atom % of carbon to silicon (C/Si) was used. The results are shown in Table 2.

Comparative Example A3

100 parts by weight of the acryl-based sticky material D obtained in Comparative Example A1, 2 parts by weight of an epoxy compound (TETRAD-C, manufactured by Mitsubishi Gas Chemical Co., Ltd.), 25 parts by weight of 2,2-dimethyl-1,3-dioxane-4,6-dione (manufactured by Wako Chemical, Ltd.), and 50 parts by weight of ethyl acetate were added to afford a sticky material composition. The obtained sticky material composition was coated onto PET having a release-treated surface to a thickness of a dried film of 20 μm using an applicator, and then heated at 100° C. for 2 minutes, and the coating solution was dried. Then, the residue was attached to the PET film and cured at 40° C. for 3 days to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes, and immediately after taking out from the hot plate, the tape was stripped. ESCA measurement was carried out in the same manner as in Example A3. The results are shown in Table 2.

TABLE 2

|  | Atom % | | | |
|---|---|---|---|---|
|  | C | O | Si | C/Si |
| Example A4 | 74.7 | 12.0 | 13.3 | 5.62 |
| Comparative Example A3 | 77.1 | 16.6 | 6.3 | 12.24 |

In Example A4 out of Example A4 and Comparative Example A3, the amount of carbon on the surface of the silicon wafer was less. From this, it can be seen that in Example A4, the amount of the organic materials attached on the silicon wafer was less than in Comparative Example A3, that is, the contamination amount was less. The ratio (C/Si) of atom % of carbon to silicon on the surface of the silicon wafer surface is preferably equal to or less than 10, more preferable equal to or less than 6, and still more preferably equal to or less than 1.

Example A5

The same procedure as in Example A1 except that 15 g of 5-(p-styrylmethyl)-2,2,5-trimethyl-1,3-dioxane-4,6-dione was changed to 5-(p-styrylmethyl)-2,2-diethyl-5-methyl-1,3-dioxane-4,6-dione synthesized in Preparation Example A7 was carried out to obtain an acryl-based sticky material composition K having a molecular weight of 300,000. The glass transition temperature was measured by differential scanning calorimetry (DSC-60, manufactured by Shimadzu Corporation) and was found to be 12° C.

100 parts by weight of the obtained acryl-based sticky material K, 2 parts by weight of an epoxy compound (TETRAD-C, manufactured by Mitsubishi Gas Chemical Company, Inc.), and 50 parts by weight of ethyl acetate were added thereto to afford a sticky material composition.

The obtained sticky material composition was coated onto PET having a release-treated surface to a thickness of a dried film of 20 μm using an applicator, and then heated at 120° C. for 5 minutes, and the coating solution was dried. Then, the residue was attached to the PET film and cured at 60° C. for 1 day to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes to confirm the expandability. After taking out from the hot plate, the tape was stripped to confirm the strippability and the adhesive residues. The results are shown in Table 3.

Example A6

10 g of 5-(p-styrylmethyl)-2,2,5-trimethyl-1,3-dioxane-4,6-dione synthesized in Preparation Example A3, 20 g of butyl acrylate, 68 g of 2-ethylhexyl acrylate, 2 g of methacrylic acid, and 100 g of ethyl acetate were added to a 500-mL 4-necked flask, and mixed at room temperature. Further, 0.2 g of 2,2'-azobisvaleronitrile was added thereto, and the mixture was heated to 75° C. and then kept to be stirred for 10 hours to obtain an acryl-based sticky material E having a molecular weight of 300,000. The glass transition temperature was measured by differential scanning calorimetry (DSC-60, manufactured by Shimadzu Corporation) and found to be −4° C.

100 parts by weight of the obtained acryl-based sticky material E, 2 parts by weight of an epoxy compound (TETRAD-C, manufactured by Mitsubishi Gas Chemical Company, Inc.), and 50 parts by weight of ethyl acetate were added thereto to afford a sticky material composition.

The obtained sticky material composition was coated onto PET having a release-treated surface to a thickness of a dried film of 20 μm using an applicator, and then heated at 120° C. for 5 minutes, and the coating solution was dried. Then, the residue was attached to the PET film and cured at 60° C. for 1 day to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes, and immediately after taking out from the hot plate, the tape was stripped to confirm the strippability and the adhesive residues according to the following criteria. The results are shown in Table 3.

Example A7

The same procedure as in Example A6 except that 10 g of 5-(p-styrylmethyl)-2,2,5-trimethyl-1,3-dioxane-4,6-dione was changed to 5-(p-styrylmethyl)-2-ethyl-2,5-dimethyl-1,3-dioxane-4,6-dione synthesized in Preparation Example A4 was carried out to obtain an acryl-based sticky material F having a molecular weight of 300,000. The glass transition temperature was measured by differential scanning calorimetry (DSC-60, manufactured by Shimadzu Corporation) and found to be −5° C.

100 parts by weight of the obtained acryl-based sticky material F, 2 parts by weight of an epoxy compound (TETRAD-C, manufactured by Mitsubishi Gas Chemical Company, Inc.), and 50 parts by weight of ethyl acetate were added thereto to afford a sticky material composition.

The obtained sticky material composition was coated onto PET having a release-treated surface to a thickness of a dried film of 20 μm using an applicator, and then heated at 120° C. for 5 minutes, and the coating solution was dried. Then, the residue was attached to the PET film and cured at 60° C. for 1 day to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes to confirm the expandability. After taking out from the hot plate, the tape was stripped to confirm the strippability and the adhesive residues. The results are shown in Table 3.

Example A8

18 g of 5-(p-styrylmethyl)-2,2,5-trimethyl-1,3-dioxane-4,6-dione synthesized in Preparation Example A3, 20 g of butyl acrylate, 60 g of 2-ethylhexyl acrylate, 2 g of methacrylic acid, and 100 g of ethyl acetate were added to a 500-mL 4-necked flask, and mixed at room temperature. Further, 0.2 g of 2,2'-azobisvaleronitrile was added thereto, and the mixture was heated to 75° C. and then kept to be stirred for 10 hours to obtain an acryl-based sticky material G having a molecular weight of 200,000. The glass transition temperature was measured by differential scanning calorimetry (DSC-60, manufactured by Shimadzu Corporation) and found to be 20° C.

100 parts by weight of the obtained acryl-based sticky material G, 2 parts by weight of an epoxy compound (TETRAD-C, manufactured by Mitsubishi Gas Chemical Company, Inc.), and 50 parts by weight of ethyl acetate were added thereto to afford a sticky material composition.

The obtained sticky material composition was coated onto PET having a release-treated surface to a thickness of a dried film of 20 μm using an applicator, and then heated at 120° C. for 5 minutes, and the coating solution was dried. Then, the residue was attached to the PET film and cured at 60° C. for 1 day to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes, and immediately after taking out from the hot plate, the tape was stripped to confirm the strippability and the adhesive residues according to the following criteria. The results are shown in Table 3.

Example A9

The same procedure as in Example A8 except that 18 g of 5-(p-styrylmethyl)-2,2,5-trimethyl-1,3-dioxane-4,6-dione was changed to 5-(p-styrylmethyl)-2-ethyl-2,5-dimethyl-1,3-dioxane-4,6-dione synthesized in Preparation Example A4 was carried out to obtain an acryl-based sticky material H having a molecular weight of 260,000. The glass transition temperature was measured by differential scanning calorimetry (DSC-60, manufactured by Shimadzu Corporation) and found to be 19° C.

100 parts by weight of the obtained acryl-based sticky material H, 2 parts by weight of an epoxy compound (TETRAD-C, manufactured by Mitsubishi Gas Chemical Company, Inc.), and 50 parts by weight of ethyl acetate were added thereto to afford a sticky material composition.

The obtained sticky material composition was coated onto PET having a release-treated surface to a thickness of a dried film of 20 μm using an applicator, and then heated at 120° C. for 5 minutes, and the coating solution was dried. Then, the residue was attached to the PET film and cured at 60° C. for 1 day to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes to confirm the expandability. After taking out from the hot plate, the tape was stripped to confirm the strippability and the adhesive residues. The results are shown in Table 3.

Example A10

15 g of 5-(p-styrylmethyl)-2,2,5-trimethyl-1,3-dioxane-4,6-dione synthesized in Preparation Example A3, 20 g of butyl acrylate, 61 g of 2-ethylhexyl acrylate, 1 g of 2-hydroxyethyl methacrylate, and 2 g of methacrylic acid, and 100 g of ethyl acetate were added to a 500-mL 4-necked flask, and mixed at room temperature. Further, 0.2 g of 2,2'-azobisvaleronitrile was added thereto, and the mixture was heated to 75° C. and then kept to be stirred for 10 hours to obtain an acryl-based sticky material I having a molecular weight of 250,000. The glass transition temperature was measured by differential scanning calorimetry (DSC-60, manufactured by Shimadzu Corporation) and found to be 15° C.

100 parts by weight of the obtained acryl-based sticky material I, 2 parts by weight of an epoxy compound (TETRAD-C, manufactured by Mitsubishi Gas Chemical Company, Inc.), and 50 parts by weight of ethyl acetate were added thereto to afford a sticky material composition.

The obtained sticky material composition was coated onto PET having a release-treated surface to a thickness of a dried film of 20 μm using an applicator, and then heated at 120° C. for 5 minutes, and the coating solution was dried. Then, the residue was attached to the PET film and cured at 60° C. for 1 day to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes, and immediately after taking out from the hot plate, the tape was stripped to confirm the strippability and the adhesive residues according to the following criteria. The results are shown in Table 3.

Example A11

The same procedure as in Example A10 except that 15 g of 5-(p-styrylmethyl)-2,2,5-trimethyl-1,3-dioxane-4,6-dione was changed to 5-(p-styrylmethyl)-2-ethyl-2,5-dimethyl-1,3-dioxane-4,6-dione synthesized in Preparation Example A4 was carried out to obtain a sticky material composition J having a molecular weight of 260,000. The glass transition temperature was measured by differential scanning calorimetry (DSC-60, manufactured by Shimadzu Corporation) and was found to be −4° C.

100 parts by weight of the obtained acryl-based sticky material J, 2 parts by weight of an epoxy compound (TETRAD-C, manufactured by Mitsubishi Gas Chemical Company, Inc.), and 50 parts by weight of ethyl acetate were added thereto to afford a sticky material composition.

The obtained sticky material composition was coated onto PET having a release-treated surface to a thickness of a dried film of 20 μm using an applicator, and then heated at 120° C. for 5 minutes, and the coating solution was dried. Then, the residue was attached to the PET film and cured at 60° C. for 1 day to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes to confirm the expandability. After taking out from the hot plate, the tape was stripped to confirm the strippability and the adhesive residues. The results are shown in Table 3.

Example A12

100 parts by weight of the acryl-based sticky material L obtained in Preparation Example A8, 10 parts by weight of 5-(p-styrylmethyl)-2,2,5-trimethyl-1,3-dioxane-4,6-dione synthesized in Preparation Example A3, 1 part by weight of IRGACURE 369 (manufactured by BASF Corporation), 1 part by weight of an epoxy compound (TETRAD-C, manufactured by Mitsubishi Gas Chemical Company, Inc.), and 50 parts by weight of ethyl acetate were added to obtain a sticky material composition.

The obtained sticky material composition was coated onto PET having a release-treated surface to a thickness of a dried film of 20 μm using an applicator, and then heated at 120° C. for 5 minutes, and the coating solution was dried. Then, the residue was attached to the PET film, irradiated with UV (1400 mJ) with a UV irradiator to perform chemical bonding, and then cured at 60° C. for 1 day to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes, and immediately after taking out from the hot plate, the tape was stripped to confirm the strippability and the adhesive residues according to the following criteria. The results are shown in Table 3.

Example A13

The same procedure as in Example A12 except that 10 parts by weight of 5-(p-styrylmethyl)-2,2,5-trimethyl-1,3-dioxane-4,6-dione was changed to 15 parts by weight was carried out to afford a sticky material composition.

The obtained sticky material composition was coated onto PET having a release-treated surface to a thickness of a dried film of 20 μm using an applicator, and then heated at 120° C. for 5 minutes, and the coating solution was dried. Then, the residue was attached to the PET film, irradiated with UV (1400 mJ) with a UV irradiator, and cured at 60° C. for 1 day to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes, and immediately after taking out from the hot plate, the tape was stripped to confirm the strippability and the adhesive residues according to the following criteria. The results are shown in Table 3.

TABLE 3

| | Strippability | Adhesive residue |
|---|---|---|
| Example A5 | ○ | ○ |
| Example A6 | ○ | ○ |
| Example A7 | ○ | ○ |
| Example A8 | ○ | ○ |
| Example A9 | ○ | ○ |
| Example A10 | ○ | ○ |
| Example A11 | ○ | ○ |
| Example A12 | ○ | ○ |
| Example A13 | ○ | ○ |

Example 2

Preparation Example B1

100 g of methylmalonic acid (manufactured by Tokyo Chemical Industry Co., Ltd.) and 100 g of acetic anhydride were charged into a 500-mL 4-necked flask. 0.5 g of 98% sulfuric acid was subsequently charged to the flask, and then 75 g of methylethylketone was added dropwise thereto over 1 hour with a dropping funnel. After stirring at room temperature for 24 hours, 200 g of ethyl acetate and 300 g of distilled water were added thereto to carry out extraction of the organic layer with a separating funnel. The solvent was evaporated from the obtained organic layer with an evaporator to obtain 75 g of 2-ethyl-2,5-dimethyl-1,3-dioxane-4,6-dione. $H^1$ NMR (300 MHz) was measured and the following peaks were obtained. $\delta=1.04$-$1.12$ (m, 3H), 1.57-1.61 (m, 3H), 1.71 (s, 1.12H), 1.77 (s, 1.92H), 1.95-2.16 (m, 2H), 3.53-5.65 (m, 1H)

Preparation Example B2

The same procedure as in Preparation Example B1 except that 75 g of methylethylketone in Preparation Example B1 was changed to 80 g of cyclopentanone was carried out to obtain 80 g of 8-methyl-6,10-dioxaspiro[4,5]decane-7,9-dione $H^1$ NMR (300 MHz) was measured and the following peaks were obtained. $\delta=1.53$ (d, 5.4 Hz, 3H), 1.84-1.97 (m, 4H), 2.21-2.27 (m, 4H), 3.63 (q, 5.4 Hz, 1H)

Preparation Example B3

100 g of 2,2-dimethyl-1,3-dioxane-4,6-dione (manufactured by Tokyo Chemical Industry Co., Ltd.) and 100 g of dimethyl formamide were charged into a 500-mL 4-necked flask. 200 g of potassium carbonate was subsequently charged to the flask, and then 197 g of methyl iodide was added dropwise thereto over 1 hour with a dropping funnel. After stirring at 40° C. for 12 hours, 300 g of ethyl acetate was added thereto and the solid produced was separated by filtration by Nutsche. Washing was carried out twice with a separating funnel using 300 mL of distilled water and then the solvent was evaporated with an evaporator to obtain 114.8 g of 2,2,5,5-tetramethyl-1,3-dioxane-4,6-dione. $H^1$ NMR (300 MHz) was measured and the following peaks were obtained. $\delta=1.65$ (s, 3H), 1.76 (s, 3H)

Preparation Example B4

100 g of 2,2,5-trimethyl-1,3-dioxane-4,6-dione (manufactured by Tokyo Chemical Industry Co., Ltd.) and 100 g of dimethyl formamide were charged into a 500-mL 4-necked flask. 100 g of potassium carbonate was subsequently charged to the flask, and then 108 g of benzyl bromide was added dropwise thereto over 1 hour with a dropping funnel. After stirring at 40° C. for 12 hours, 300 g of ethyl acetate was added thereto and the solid produced was separated by filtration by Nutsche. Washing was carried out twice with a separating funnel using 300 mL of distilled water and then the solvent was evaporated with an evaporator to obtain 145 g of 5-benzyl-2,2,5-trimethyl-1,3-dioxane-4,6-dione. $H^1$ NMR (300 MHz) was measured and the following peaks were obtained. $\delta=0.97$ (s, 3H), 1.60 (s, 3H), 1.75 (s, 3H), 3.31 (s, 2H), 6.80-7.42 (m, 5H)

Preparation Example B5

100 g of 2-ethyl-2,5-dimethyl-1,3-dioxane-4,6-dione synthesized in Preparation Example B1 and 100 g of dimethyl formamide were charged into a 500-mL 4-necked flask. 100 g of potassium carbonate was subsequently charged to the flask, and then 81.5 g of methyl iodide was added dropwise thereto over 1 hour with a dropping funnel. After stirring at 40° C. for 12 hours, 300 g of ethyl acetate was added thereto and the solid produced was separated by filtration by Nutsche. Washing was carried out twice with a separating funnel using 300 mL of distilled water and then the solvent was evaporated with an evaporator to obtain 130 g of 2-ethyl-2,5,5-trimethyl-1,3-dioxane-4,6-dione. $H^1$ NMR (300 MHz) was measured and the following peaks were obtained. $\delta=1.15$ (t, 8.1 Hz, 3H), 1.65 (s, 6H), 2.00 (q, 8.1 Hz, 2H)

Preparation Example B6

The same procedure as in Preparation Example B5 except that 100 g of 2-ethyl-2,5-dimethyl-1,3-dioxane-4,6-dione was changed to 93.5 g of 8-methyl-6,10-dioxaspiro[4,5]decane-7,9-dione was carried out to obtain 80 g of 8,8-dimethyl-6,10-dioxaspiro[4,5]decane-7,9-dione. $H^1$ NMR (300 MHz) was measured and the following peaks were obtained. $\delta=1.50$ (s, 6H), 1.84-1.97 (m, 4H), 2.21-2.27 (m, 4H)

Preparation Example B7

100 g of 2-ethyl-2,5-dimethyl-1,3-dioxane-4,6-dione in Preparation Example B1 and 100 g of dimethyl formamide were charged into a 500-mL 4-necked flask.

100 g of potassium carbonate was subsequently charged to the flask, and then 108 g of benzyl bromide was added dropwise thereto over 1 hour with a dropping funnel. After stirring at 40° C. for 12 hours, 300 g of ethyl acetate was added thereto and the solid produced was separated by filtration by Nutsche. Washing was carried out twice with a separating funnel using 300 mL of distilled water and then the solvent was evaporated with an evaporator to obtain 140 g of 5-benzyl-2-ethyl-2,5-dimethyl-1,3-dioxane-4,6-dione. $H^1$ NMR (300 MHz) was measured and the following peaks were obtained. δ=0.40 (t, 8.1 Hz, 3H), 0.94 (t, 8.1 Hz, 3H), 1.14 (q, 8.1 Hz, 2H), 1.74 (s, H), 1.81 (q, 8.1 Hz, 2H), 3.31 (s, 2H), 6.80-7.42 (m, 5H)

Preparation Example B8

The same procedure as in Preparation Example B7 except that 100 g of 2-ethyl-2,5-dimethyl-1,3-dioxane-4,6-dione was changed to 93.5 g of 8-methyl-6,10-dioxaspiro[4,5]decane-7,9-dione was carried out to obtain 140 g of 8-benzyl-8-methyl-6,10-dioxaspiro[4,5]decane-7,9-dione. $H^1$ NMR (300 MHz) was measured and the following peaks were obtained. δ=1.28-1.38 (m, 2H), 1.56-1.82 (m, 4H), 1.74 (s, 3H), 2.00-2.05 (m, 2H), 3.32 (s, 2H), 6.80-7.42 (m, 5H)

Preparation Example B9

The same procedure as in Preparation Example B1 except that 75 g of methylethylketone in Preparation Example B1 was changed to 80 g of diethylketone was carried out to obtain 80 g of 2,2-diethyl-5-methyl-1,3-dioxane-4,6-dione. $H^1$ NMR (300 MHz) was measured and the following peaks were obtained. δ=1.04 (q, 8.1 Hz, 6H), 1.58 (d, 7.8 Hz, 3H), 1.96 (s, 8.1 Hz, 2H), 2.05 (s, 8.1 Hz, 2H), 3.57 (q, 5.4 Hz, 1H)

Preparation Example B10

According to Preparation Example B5 except that 100 g of 2-ethyl-2,5-dimethyl-1,3-dioxane-4,6-dione was changed to 85 g of 2,2-diethyl-5-methyl-1,3-dioxane-4,6-dione synthesized in Preparation Example B9 was carried out to obtain 95 g of 2,2-diethyl-5,5-dimethyl-1,3-dioxane-4,6-dione. $H^1$ NMR (300 MHz) was measured and the following peaks were obtained. δ=1.15 (t, 8.1 Hz, 6H), 1.65 (s, 6H), 2.00 (q, 8.1 Hz, 4H)

Preparation Example B11

According to Preparation Example B7 except that 100 g of 2-ethyl-2,5-dimethyl-1,3-dioxane-4,6-dione was changed to 85 g of 2,2-diethyl-5-methyl-1,3-dioxane-4,6-dione synthesized in Preparation Example B9 was carried out to obtain 95 g of 5-benzyl-2,2-diethyl-5-methyl-1,3-dioxane-4,6-dione. $H^1$ NMR (300 MHz) was measured and the following peaks were obtained. δ=0.40 (t, 8.1 Hz, 3H), 0.94 (t, 8.1 Hz, 3H), 1.14 (q, 8.1 Hz, 2H), 1.70 (s, 3H), 1.80 (q, 8.1 Hz, 2H), 3.31 (s, 2H), 7.10-7.50 (m, 5H)

Preparation Example B12

100 g of 2,2,5-trimethyl-1,3-dioxane-4,6-dione (manufactured by Tokyo Chemical Industry Co., Ltd.) and 100 g of dimethyl formamide were charged into a 500-mL 4-necked flask. 95 g of potassium carbonate was subsequently charged to the flask, and then 97 g of 4-chloromethylstyrene was added dropwise thereto over 1 hour with a dropping funnel. After stirring at 40° C. for 24 hours, 400 g of ethyl acetate was added thereto and the solid produced was separated by filtration by Nutsche. Washing was carried out twice with a separating funnel using 300 mL of distilled water and then the solvent was evaporated with an evaporator to obtain 150 g of 5-(p-styrylmethyl)-2,2,5-trimethyl-1,3-dioxane-4,6-dione. $H^1$ NMR (300 MHz) was measured and the following peaks were obtained. δ=0.97 (s, 3H), 1.60 (s, 3H), 1.75 (s, 3H), 3.31 (s, 2H), 5.22 (d, 12.0 Hz, 1H), 5.70 (d, 19.5 Hz, 1H), 6.65 (dd, 12.0, 19.5 Hz, 1H), 7.13 (d, 9.0 Hz, 2H), 7.31 (d, 9.0 Hz, 2H)

Reference Example B1

80 g of butyl acrylate, 15 g of ethyl acrylate, 5 g of methacrylic acid, and 100 g of ethyl acetate were added to a 500-mL 4-necked flask and mixed at room temperature. Further, 0.2 g of 2,2'-azobisvaleronitrile was added thereto, and the mixture was heated to 75° C. and then kept to be stirred for 10 hours to obtain an acryl-based sticky material A having a molecular weight of 400,000. The glass transition temperature was measured by differential scanning calorimetry (DSC-60, manufactured by Shimadzu Corporation) and found to be −40° C.

Reference Example B2

15 g of 5-(p-styrylmethyl)-2,2,5-trimethyl-1,3-dioxane-4,6-dione synthesized in Preparation Example B12, 20 g of butyl acrylate, 63 g of 2-ethylhexyl acrylate, 2 g of methacrylic acid, and 100 g of ethyl acetate were added to a 500-mL 4-necked flask and mixed at room temperature. Further, 0.2 g of 2,2'-azobisvaleronitrile was added thereto, and the mixture was heated to 75° C. and then kept to be stirred for 10 hours to obtain an acryl-based sticky material B having a molecular weight of 300,000. The glass transition temperature was measured by differential scanning calorimetry (DSC-60, manufactured by Shimadzu Corporation) and found to be 14° C.

Example B1

100 parts by weight of the acryl-based sticky material A obtained in Reference Example B1, 1.5 parts by weight of an epoxy compound (TETRAD-C, manufactured by Mitsubishi Gas Chemical Company, Inc.), 25 parts by weight of 2,2-dimethyl-1,3-dioxane-4,6-dione, and 50 parts by weight of ethyl acetate were added thereto to afford a sticky material composition. The obtained sticky material composition was coated onto PET having a release-treated surface to a thickness of a dried film of 20 μm using an applicator, and then heated at 100° C. for 2 minutes, and the coating solution was dried. Then, the residue was attached to the PET film and cured at 60° C. for 3 days to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes, and immediately after taking out from the hot plate, the tape was stripped to confirm the strippability and the adhesive residues according to the following criteria. The results are shown in Table 4.

(Strippability)

After the tape was vacuum-chucked, the tape was lift vertically to carry out the stripping. A case of being stripped was indicated as o and a case of being not stripped was indicated as x.

(Adhesive Residue)

After the stripping, the SUS plate was visually observed and determined. A case where even a little adhesive residue was recognized was indicated as x.

Examples B2 to B10

The test was carried out in the same manner as in Example B1 except that 25 parts by weight of 2,2-dimethyl-1,3-dioxane-4,6-dione was changed to 25 parts by weight of the compound shown in Tables. The results are shown in Table 4.

Comparative Example B1

100 parts by weight of the acryl-based sticky material A obtained in Reference Example B1, 2 parts by weight of an epoxy compound (TETRAD-C, manufactured by Mitsubishi Gas Chemical Company, Inc.), 25 parts by weight of 2,2'-azobis-(N-butyl-2-methylpropionamide), and 50 parts by weight of ethyl acetate were added thereto to afford a sticky material composition. The obtained sticky material composition was coated onto PET having a release-treated surface to a thickness of a dried film of 20 μm using an applicator, and then heated at 100° C. for 2 minutes, and the coating solution was dried. Then, the residue was attached to the PET film and cured at 40° C. for 3 days to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes, and immediately after taking out from the hot plate, the tape was stripped to confirm the strippability and the adhesive residues. The results are shown in Table 4.

Comparative Example B2

100 parts by weight of the acryl-based sticky material A obtained in Reference Example B1, 2 parts by weight of an epoxy compound (TETRAD-C, manufactured by Mitsubishi Gas Chemical Company, Inc.), 25 parts by weight of Matsumoto Microsphere FN-180 (thermally expandable microcapsule, manufactured by Matsumoto Yushi-Seiyaku Co., Ltd.), and 50 parts by weight of ethyl acetate were added thereto to afford a sticky material composition. The obtained sticky material composition was coated onto PET having a release-treated surface to a thickness of a dried film of 20 μm using an applicator, and then heated at 100° C. for 2 minutes, and the coating solution was dried. Then, the residue was attached to the PET film and cured at 40° C. for 3 days to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes, and immediately after taking out from the hot plate, the tape was stripped to confirm the strippability and the adhesive residues. The results are shown in Table 4.

TABLE 4

|  |  | $R^1$ | $R^2$ | $R^3$ | $R^4$ | Strippability | Adhesive residue |
|---|---|---|---|---|---|---|---|
| Example B1 |  | H | H | Me | Me | o | o |
| Example B2 |  | H | Me | Me | Me | o | o |
| Example B3 | Preparation Example B3 | Me | Me | Me | Me | o | o |
| Example B4 | Preparation Example B4 | Me | PhCH$_2$ | Me | Me | o | o |
| Example B5 | Preparation Example B1 | H | Me | Me | CH$_2$CH$_3$ | o | o |
| Example B6 | Preparation Example B5 | Me | Me | Me | CH$_2$CH$_3$ | o | o |
| Example B7 | Preparation Example B7 | Me | PhCH$_2$ | Me | CH$_2$CH$_3$ | o | o |
| Example B8 | Preparation Example B2 | H | Me | CH$_2$CH$_2$CH$_2$CH$_2$ | | o | o |
| Example B9 | Preparation Example B6 | Me | Me | CH$_2$CH$_2$CH$_2$CH$_2$ | | o | o |
| Example B10 | Preparation Example B8 | Me | PhCH$_2$ | CH$_2$CH$_2$CH$_2$CH$_2$ | | o | o |
| Comparative Example B1 | 2,2'-Azobis-(N-butyl-2-methylpropionamide) | | | | | o | x |
| Comparative Example B2 | Matsumoto Microsphere FN-180 | | | | | o | x |

* In the Table, in the case where $R^3$ and $R^4$ represent "CH$_2$CH$_2$CH$_2$CH$_2$", they are combined with carbon atoms to which $R^3$ and $R^4$ are bonded to represent a cyclopentyl group.

Example B2

2,2,5-Trimethyl-1,3-dioxane-4,6-dione

Examples B11 to B14

The test was carried out in the same manner as in Example B1 except that 25 parts by weight of 2,2-dimethyl-1,3-dioxane-4,6-dione was changed to 25 parts by weight of the compound shown in Table 5. The results are shown in Table 5.

TABLE 5

|  |  | R¹ | R² | R³ | R⁴ | Strippability | Adhesive residue |
|---|---|---|---|---|---|---|---|
| Example B11 | Preparation Example B9 | H | Me | Et | Et | ○ | ○ |
| Example B12 | Preparation Example B10 | Me | Me | Et | Et | ○ | ○ |
| Example B13 | Preparation Example B11 | Me | PhCH₂ | Et | Et | ○ | ○ |
| Example B14 | Preparation Example B12 | Me | CH₂=CH-C₆H₄-CH₂ | Me | Me | ○ | ○ |

Example B15

100 parts by weight of the acryl-based sticky material B obtained in Reference Example B2, 1.5 parts by weight of an epoxy compound (TETRAD-C, manufactured by Mitsubishi Gas Chemical Company, Inc.), 25 parts by weight of 2,2-dimethyl-1,3-dioxane-4,6-dione, and 50 parts by weight of ethyl acetate were added thereto to afford a sticky material composition. The obtained sticky material composition was coated onto PET having a release-treated surface to a thickness of a dried film of 20 μm using an applicator, and then heated at 100° C. for 2 minutes, and the coating solution was dried. Then, the residue was attached to the PET film and cured at 60° C. for 3 days to afford a sticky tape. The obtained film was attached to an SUS plate, in which a PET side having a release-treated surface had been stripped and mirror-finished, with a roller, and left to stand for 1 hour. Heating was carried out on a hot plate at 180° C. for 3 minutes, and immediately after taking out from the hot plate, the tape was stripped to confirm the strippability and the adhesive residues according to the following criteria. The results are shown in Table 6.

Examples B16 to B20

The test was carried out in the same manner as in Example B15 except that 25 parts by weight of 2,2-dimethyl-1,3-dioxane-4,6-dione was changed to 25 parts by weight of the compound shown in Table 6. The results are shown in Table 6.

This application claims the priority benefit based on Japanese Patent Application No. 2011-273689 filed on Dec. 14, 2011, Japanese Patent Application No. 2011-273692 filed on Dec. 14, 2011, Japanese Patent Application No. 2012-157250 filed on Jul. 13, 2012, and Japanese Patent Application No. 2012-157251 filed on Jul. 13, 2012, each disclosure of which is hereby incorporated by reference in its entirety.

The invention claimed is:

1. An adhesive resin composition comprising an expandable sticky polymer formed from a Meldrum's acid derivative, wherein the expandable sticky polymer includes:
   (a) a constituent unit derived from the Meldrum's acid derivative represented by the formula (1); and
   (b) a constituent unit derived from a (meth)acrylic acid derivative,

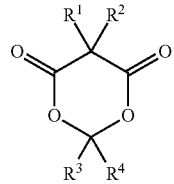

(1)

wherein R¹ and R² each independently represent a hydrogen atom, a halogen atom, a substituted or unsubstituted alkyl group having 1 to 10 carbon atoms, a substituted or unsubstituted alkenyl group having 2 to

TABLE 6

|  |  | R¹ | R² | R³ | R⁴ | Strippability | Adhesive residue |
|---|---|---|---|---|---|---|---|
| Example B15 |  | H | H | Me | Me | ○ | ○ |
| Example B16 | Preparation Example B1 | H | Me | Me | CH₂CH₃ | ○ | ○ |
| Example B17 | Preparation Example B4 | Me | PhCH₂ | Me | Me | ○ | ○ |
| Example B18 | Preparation Example B6 | Me | Me | CH₂CH₂CH₂CH₂ |  | ○ | ○ |
| Example B19 | Preparation Example B11 | Me | PhCH₂ | Et | Et | ○ | ○ |
| Example B20 | Preparation Example B12 | Me | CH₂=CH-C₆H₄-CH₂ | Me | Me | ○ | ○ |

*In the Table, in the case where R³ and R⁴ represent "CH₂CH₂CH₂CH₂", they are combined with carbon atoms to which R³ and R⁴ are bonded to represent a cyclopentyl group.

10 carbon atoms, a substituted or unsubstituted alkynyl group having 2 to 10 carbon atoms, a substituted or unsubstituted aryl group, a substituted or unsubstituted arylalkyl group having 7 to 12 carbon atoms, or a substituted or unsubstituted silyl group, and $R^1$ and $R^2$ may be bonded to each other to form a ring structure; $R^3$ and $R^4$ each independently represent a hydrogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, or a substituted or unsubstituted aryl group, and $R^3$ and $R^4$ may be bonded to each other to form a ring structure; with the proviso that at least one of $R^1$, $R^2$, $R^3$ and $R^4$ is a benzyl group having a vinyl group as a substituent.

2. The adhesive resin composition according to claim 1, wherein the expandable sticky polymer includes an adhesive resin having the Meldrum's acid derivative bonded through a reactive functional group included in the Meldrum's acid derivative.

3. The adhesive resin composition according to claim 1, wherein the glass transition temperature measured by differential scanning calorimetry is equal to or lower than 40° C.

4. A laminate comprising:
a base material;
a strippable layer including the adhesive resin composition according to claim 1, formed on the base material; and
an adherend adhered to the strippable layer.

5. A self-stripping method using a laminate including a base material, a strippable layer having the adhesive resin composition according to claim 1, formed on the base material, and an adherend adhered to the strippable layer, the method comprising:
a step of heating the laminate to equal to or higher than a temperature at which the Meldrum's acid derivative included in the adhesive resin composition is decomposed, thereby decomposing the compound included in the strippable layer, and reducing the adhesion strength of the strippable layer at the interface between the strippable layer and the adherend.

6. A tape comprising:
a base material layer; and
a strippable layer including the adhesive resin composition according to claim 1, formed on the base material layer.

7. A method for polishing a substrate, comprising:
a step of attaching the tape according to claim 6 to the backside of a surface to be polished of the substrate through the strippable layer;
a step of polishing the surface to be polished in the substrate; and
a step of stripping the tape from the backside by applying heat to the strippable layer of the tape after the polishing step.

8. A dicing method comprising:
a step of fixing an adherend onto a support by the adhesive resin composition according to claim 1;
a step of dicing the adherend; and
a step of stripping the adherend, which has been made into individual pieces by applying heat, from the support.

9. A method for preparing a semiconductor package, comprising:
a step of fixing a semiconductor chip onto a support by the adhesive resin composition according to claim 1;
a step of sealing the semiconductor chip with a resin; and
a step of stripping the semiconductor chip sealed with the resin from the support by applying heat.

10. A plating method comprising:
a step of attaching the tape according to claim 6 to a portion not to be plated in a body to be plated, through the strippable layer;
a step of subjecting the body to be plated to a plating treatment; and
a step of stripping the tape by applying heat to the strippable layer of the tape attached to the body to be plated after the plating treatment step.

11. An adhesive resin composition comprising:
a Meldrum's acid derivative represented by the following general formula (1):

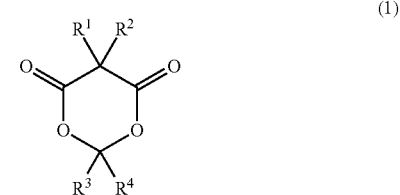

wherein $R^1$ and $R^2$ each independently represent a hydrogen atom, a halogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aryl group, a substituted or unsubstituted arylalkyl group having 7 to 12 carbon atoms, or a substituted or unsubstituted silyl group, and $R^1$ and $R^2$ may be bonded to each other to form a ring structure; $R^3$ and $R^4$ each independently represent a hydrogen atom, a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, or a substituted or unsubstituted aryl group, and $R^3$ and $R^4$ may be bonded to each other to form a ring structure; with the proviso that at least one of $R^1$, $R^2$, $R^3$ and $R^4$ is a benzyl group having a vinyl group as a substituent; and
an adhesive resin.

12. The adhesive resin composition according to claim 11, wherein in the general formula (1), $R^1$ and $R^2$ each independently represent a hydrogen atom, an alkyl group having 1 to 4 carbon atoms, or a benzyl group having a vinyl group as a substituent, $R^3$ and $R^4$ each independently represent a hydrogen atom or an alkyl group having 1 to 4 carbon atoms, or $R^3$ and $R^4$ are bonded to each other to form a cyclopentyl group.

13. The adhesive resin composition according to claim 11, wherein the adhesive resin has a glass transition temperature measured by differential scanning calorimetry of equal to or lower than 40° C.

14. The adhesive resin composition according to claim 11, wherein the adhesive resin is an acryl-based pressure sensitive adhesive.

15. A self-stripping method using a laminate including a base material, a strippable layer having the adhesive resin composition according to claim 11, formed on the base material, and an adherend adhered to the strippable layer, the method comprising:

a step of heating the laminate to equal to or higher than a temperature at which the Meldrum's acid derivative is decomposed, and decomposing the Meldrum's acid derivative included in the strippable layer, thereby reducing the adhesion strength of the strippable layer at the interface between the strippable layer and the adherend.

* * * * *